(12) United States Patent
Chinn et al.

(10) Patent No.: US 8,377,461 B2
(45) Date of Patent: Feb. 19, 2013

(54) MULTIFUNCTIONAL MEDICAL ARTICLES

(75) Inventors: Joseph A. Chinn, Shakopee, MN (US);
Sean M. Stucke, Farmington, MN (US);
Stephen J. Chudzik, St. Paul, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1816 days.

(21) Appl. No.: 11/295,836

(22) Filed: Dec. 6, 2005

(65) Prior Publication Data

US 2007/0003588 A1 Jan. 4, 2007

Related U.S. Application Data

(60) Provisional application No. 60/633,841, filed on Dec. 6, 2004.

(51) Int. Cl.
*A61F 2/00* (2006.01)
*A61F 13/00* (2006.01)
*A61K 9/14* (2006.01)
*A61K 31/727* (2006.01)

(52) U.S. Cl. ........ 424/423; 424/422; 424/484; 424/486; 514/56

(58) Field of Classification Search .................. 424/423, 424/422, 484, 486; 514/56
See application file for complete search history.

(56) References Cited

U.S. PATENT DOCUMENTS

| | | | |
|---|---|---|---|
| 5,002,582 A | 3/1991 | Guire et al. | |
| 5,414,075 A | 5/1995 | Swan et al. | |
| 5,563,056 A | 10/1996 | Swan et al. | |
| 5,637,460 A | 6/1997 | Swan et al. | |
| 5,714,360 A | 2/1998 | Swan et al. | |
| 5,744,515 A | 4/1998 | Clapper | |
| 5,902,631 A | 5/1999 | Wang et al. | |
| 6,007,833 A | 12/1999 | Chudzik et al. | |
| 6,048,620 A | 4/2000 | Zhong | |
| 6,077,698 A | 6/2000 | Swan et al. | |
| 6,096,070 A | 8/2000 | Ragheb et al. | |
| 6,278,018 B1 | 8/2001 | Swan | |
| 6,299,604 B1 | 10/2001 | Ragheb et al. | |
| 6,315,794 B1 * | 11/2001 | Richter | 623/1.34 |
| 6,410,044 B1 | 6/2002 | Chudzik et al. | |
| 6,514,734 B1 * | 2/2003 | Clapper et al. | 435/180 |
| 6,603,040 B1 | 8/2003 | Swan | |
| 6,659,959 B2 * | 12/2003 | Brockway et al. | 600/488 |
| 6,663,662 B2 | 12/2003 | Pacetti et al. | |
| 2001/0003796 A1 | 6/2001 | Yang et al. | |
| 2003/0083646 A1 | 5/2003 | Sirhan et al. | |
| 2003/0162032 A1 | 8/2003 | Zhong et al. | |
| 2004/0034337 A1 | 2/2004 | Boulais et al. | |
| 2004/0062875 A1 | 4/2004 | Chappa et al. | |
| 2004/0137164 A1 | 7/2004 | Swan et al. | |
| 2004/0202774 A1 | 10/2004 | Chudzik et al. | |
| 2004/0210208 A1 | 10/2004 | Paul et al. | |
| 2005/0100580 A1 | 5/2005 | Osborne et al. | |
| 2005/0154452 A1 | 7/2005 | Hezi-Yamit et al. | |
| 2005/0154455 A1 | 7/2005 | Hezi-Yamit et al. | |
| 2005/0228490 A1 | 10/2005 | Hezi-Yamit et al. | |
| 2005/0239508 A1 | 10/2005 | Schwarz et al. | |

FOREIGN PATENT DOCUMENTS

| | | |
|---|---|---|
| CH | 649 916 A5 | 6/1985 |
| EP | 1 174 157 | 1/2002 |
| EP | 1360967 | 11/2003 |
| GB | 2 202 762 | 10/1988 |
| WO | WO 98/35717 | 8/1998 |
| WO | WO 2004/093962 | 11/2004 |
| WO | WO 2006/023859 | 3/2006 |

OTHER PUBLICATIONS

International Search Report, (4 pgs) May 11, 2006.

\* cited by examiner

*Primary Examiner* — Abigail Fisher
(74) *Attorney, Agent, or Firm* — Kagan Binder, PLLC

(57) ABSTRACT

The invention provides medical articles that include more than one biocompatibility-promoting function. In one aspect, the invention provides a medical articles that include a polymeric matrix including more than one biocompatible agent, wherein each biocompatible agent is provided at a distinct portion of the medical article surface. Methods of making medical articles, as well as methods of using the same, are also described.

36 Claims, 3 Drawing Sheets

Friction Data: Biocompatible Agent Including Polymerizable Groups versus Hydrophilic Base Coat Only

| Cycle | uncoated | Average Frictional Force Generated (g) | | | | | | | | | |
|---|---|---|---|---|---|---|---|---|---|---|---|
| | | Collagen Macromer | | | | | Hydrophilic Base coat only | | | | |
| | | cm1 | cm2 | cm3 | cm4 | cm5 | TF1 | TF2 | TF3 | TF4 | TF5 |
| 1 | -229.0 | -6.5 | -18.9 | -10.3 | -11.9 | -5.6 | -2.1 | -5.5 | -3.3 | -4.9 | -8.8 |
| 2 | -199.4 | -5.9 | -16.5 | -10.0 | -10.6 | -5.1 | -2.7 | -6.1 | -4.1 | -5.6 | -7.7 |
| 3 | -216.9 | -5.8 | -16.6 | -9.9 | -10.6 | -5.0 | -2.6 | -7.1 | -4.5 | -5.6 | -7.8 |
| 4 | -217.2 | -5.9 | -9.2 | -9.9 | -10.4 | -5.1 | -2.8 | -7.0 | -5.1 | -6.1 | -8.1 |
| 5 | -233.1 | -5.6 | -9.0 | -10.2 | -10.3 | -5.0 | ** | -6.7 | -6.1 | -6.2 | -7.7 |
| 6 | -215.4 | -5.4 | -8.6 | -10.0 | -10.4 | -5.0 | -2.7 | -6.6 | -6.3 | -6.1 | -7.4 |
| 7 | -226.5 | -5.5 | -8.4 | -10.1 | -10.3 | -4.9 | -2.8 | -6.4 | -6.1 | -6.0 | -7.2 |
| 8 | -230.5 | -5.5 | -8.2 | -10.0 | -10.4 | -4.9 | ** | -6.2 | -6.0 | -6.2 | -7.0 |
| 9 | -232.8 | -5.6 | -8.5 | -10.1 | -10.4 | -5.1 | -2.5 | -6.2 | -5.8 | -5.8 | -7.0 |
| 10 | -249.8 | -5.4 | -8.0 | -10.3 | -10.4 | -5.0 | -2.4 | -6.3 | -5.8 | -6.3 | -6.9 |
| 11 | -239.3 | -5.3 | -8.2 | -10.1 | -10.2 | -5.0 | -2.6 | -6.2 | -5.8 | -5.9 | -6.8 |
| 12 | -219.5 | -5.3 | -8.1 | -10.2 | -10.2 | -5.0 | -2.3 | -6.0 | -5.7 | -5.9 | -6.7 |
| 13 | -221.3 | | | -10.5 | -10.1 | -5.0 | -2.4 | -6.1 | -5.7 | -6.4 | -6.7 |
| 14 | -227.7 | | | -10.6 | -10.1 | -5.0 | -2.5 | -6.1 | -5.6 | -6.0 | -6.6 |
| 15 | -242.0 | | | -10.8 | -10.3 | -4.9 | -2.6 | -6.0 | -5.6 | -6.0 | -6.6 |

Figure 1

MULTIFUNCTIONAL MEDICAL ARTICLES

CROSS-REFERENCE TO RELATED APPLICATIONS

The present non-provisional Application claims the benefit of commonly owned provisional Application having Ser. No. 60/633,841 filed on Dec. 6, 2004, and entitled MULTIFUNCTIONAL IMPLANTABLE DEVICE.

FIELD OF THE INVENTION

The invention relates to medical articles that include more than one biocompatibility-promoting function. The inventive articles and methods find particular utility for applications in which a medical article, such as a medical device, encounters multiple physiological environments and/or conditions (such as bodily fluids or tissues) during use.

BACKGROUND OF THE INVENTION

Developments in medicine have enabled the use of many non-classical surgical techniques in the treatment of diseases and disorders. For example, significant advances in implantable medical devices have enabled a host of new treatment options for patients. Early implantable medical devices were limited to surgical grade metals and were primarily used for gross mechanical repairs such as bone securement or replacement. However, in the last two decades, implantation of temporary or permanent structural and functioning elements has become commonplace, and such devices have become more intricate and complex in their structure and function.

While beneficial for treating a variety of medical conditions, the placement of metal or polymeric devices in the body can give rise to numerous complications. Some of these complications include increased risk of infection, initiation of a foreign body response (which can result in inflammation and/or fibrous encapsulation), and initiation of a wound healing response (which can result in hyperplasia).

One approach to reducing potential complications has been to explore the types of materials used to fabricate implantable medical devices. For example, implantable medical devices can be fabricated from polymeric materials (such as polyurethane) that are believed to be less likely to initiate adverse effects within the body.

Another approach to reducing the potential harmful effects that can result from medical device implantation is to provide biocompatible agents at tissue or blood-contacting surfaces of the implanted device. For example, heparin can be provided at a surface of a device to reduce thrombogenicity. One benefit of providing biocompatible agents at the surface of a device is the avoidance of toxic concentrations of drugs that are sometimes necessary, when given systemically, to achieve therapeutic concentrations at the site where they are required.

The term "implantation site" refers to the site within a patient's body at which the implantable device is placed according to the invention. This can be compared to the term "treatment site," which can include the implantation site as well as the area of the body that is to receive treatment directly or indirectly from a device component. For example, in some instances, agents can migrate from the implantation site to areas surrounding the device itself, thereby treating a larger area than simply the implantation site. An example that illustrates this distinction can be seen in the use of drug-eluting stents (DES). These relatively recent devices can include bioactive agents that are eluted from the stent over time. Such eluted bioactive agents can provide treatment to the area of the body at the implantation site and beyond (the treatment site) as the agents migrate from the implantation site to areas surrounding the device itself.

Some treatments can require that a medical device, once implanted, reside in different physiological mileux within the body. In other words, once implanted, the device can come in contact with more than one distinct physiological environment. For example, one portion of the device may reside within a blood-contacting environment, while another portion of the device may reside within an extravascular environment, such as a tissue environment. The biocompatibility requirements for these different portions can be widely divergent.

On a separate subject, matrices that can be used for cell immobilization, tissue adherence, and controlled drug delivery in association with implantable devices have been described. See U.S. Pat. No. 6,007,833 (Chudzik et al., "Crosslinkable Macromers Bearing Initiator Groups"), U.S. Pat. No. 6,156,345 (Chudzik et al., "Crosslinkable Macromers Bearing Initiator Groups"), U.S. Pat. No. 6,410,044 (Chudzik et al., "Crosslinkable Macromers"), and U.S. Publication No. 2003/0031697 (Chudzik et al., "Crosslinkable Macromers").

SUMMARY OF THE INVENTION

Generally, the invention provides medical articles that include more than one biocompatibility-promoting function. The inventive articles and methods find particular utility for applications in which a medical article (for example, an implantable device) encounters multiple physiological environments and/or conditions (such as bodily tissues, fluids, and the like) during use. According to some aspects of the invention, devices are provided with biocompatible portions that accommodate the physiological environments in which the devices will reside upon implantation. The biocompatible portions are provided by associating different biocompatible agents with distinct selected portions of the device. In preferred embodiments, the biocompatible agents are nonreleasably associated with the device, such that the biocompatible agents remain at the selected surface of the device during residence of the device within the body. The biocompatible agent for a given portion of a medical device is selected to provide the desired function for that portion, to thereby achieve an improved overall biocompatibility of the device as a whole. Thus, the inventive medical articles can be thought of as multifunctional articles, in that they provide more than one biocompatible function in connection with a single implantable medical device.

In some article aspects, the invention provides a medical article comprising: (a) a body member; (b) a first biocompatible coating at a first surface portion, the first biocompatible coating comprising polymerization initiator and a first biocompatible agent, the first biocompatible agent including one or more reactive groups, one or more polymerizable groups, or a combination of one or more reactive groups and one or more polymerizable groups; and (c) a second biocompatible coating at a second surface portion, the second biocompatible coating comprising polymerization initiator and a second biocompatible agent, the second biocompatible agent including one or more reactive groups, one or more polymerizable groups, or a combination of one or more reactive groups and one or more polymerizable groups, wherein the first biocompatible agent and second biocompatible agent are immobilized at respective surface portions and are selected to provide different biocompatible functions when the surface portions are in contact with bodily fluids of a patient.

Thus, in some aspects, the invention provides a medical article that includes a polymeric matrix and more than one biocompatible agent, wherein each biocompatible agent is provided at a distinct portion of the article surface. The polymeric matrix provides a coating at the surface of the medical article, and the biocompatible agent can be associated with and incorporated into the polymeric matrix before, during, and/or after the polymeric matrix is provided to the surface of the medical article. The medical article is thus composed of a substrate, a polymeric matrix, and more than one biocompatible agent associated with the polymeric matrix. In preferred aspects, the biocompatible agent is nonreleasably associated with the polymeric matrix during residence of the device within the body and/or contact of the article with bodily fluids or tissues.

In some aspects, the polymeric matrix can be the same for each of the biocompatible agents included at the surface of the device. In other aspects, different polymeric matrices can be chosen for each biocompatible agent. In still further aspects, polymeric matrix material can be selected based upon such factors as the type of material utilized to fabricate a particular portion of the medical article, for example, when a medical article is fabricated of different materials (such as materials having different relative hydrophobic properties), and/or the physiological requirements of the article portions (such as blood contacting or tissue contacting surfaces, and the like).

In its method aspects, the invention can provide particular advantages when used to provide multifunctional medical articles. In some aspects, the invention provides methods for forming medical articles that include distinct biocompatible functions at distinct surface regions. Such methods involve the steps of identifying biocompatible functions for distinct portions of a single article, selecting biocompatible agents that are capable, upon implantation, of providing the biocompatible functions identified, and associating biocompatible agent with each distinct portion of the article, thereby forming a multifunctional medical article. A biocompatible function can be, for example, a desired cellular response, such as endothelial cell migration or proliferation. In some aspects, the inventive methods involve steps of providing an article having a surface with multiple portions, associating a polymeric matrix material with the surface, and associating more than one biocompatible agent with the polymeric matrix. The polymeric matrix can be provided in association with the entire, or less than the entire device surface, as desired. More than one type of polymeric matrix can be included at the article surface, when desired. In these embodiments, each polymeric matrix material can be associated with a distinct surface portion of the medical article.

In some method aspects, the invention provides a method for providing two or more functional surface portions on a medical article, the method comprising steps of: (a) disposing a first composition at a first surface portion of the medical article, the first composition comprising polymerization initiator and a first biocompatible agent, the first biocompatible agent including one or more reactive groups, one or more polymerizable groups, or a combination of one or more reactive groups and one or more polymerizable groups; (b) activating the polymerization initiator, reactive groups, or a combination thereof, to form a biocompatible coating layer at the first surface portion; (c) disposing a second composition at a second surface portion of the medical article, the second composition comprising polymerization initiator and a second biocompatible agent, the second biocompatible agent including one or more reactive groups, one or more polymerizable groups, or a combination of one or more reactive groups and one or more polymerizable groups; and (d) activating the polymerization initiator, reactive groups, or a combination thereof, to form a biocompatible coating layer at the second surface portion, wherein the first biocompatible agent and the second biocompatible agent are immobilized at respective surface portions and are selected to provide different biocompatible functions when the surface portions are in contact with bodily fluids of a patient.

In some method aspects, the inventive methods can advantageously be accomplished in a minimal amount of processing steps. According to the invention, the polymeric matrix and biocompatible agent can be applied to the medical article surface simultaneously or sequentially, as desired. In some embodiments, the polymeric matrix material is applied to the article surface in a first step, followed by application of biocompatible agent to the polymeric matrix. In other embodiments, a coating solution containing both the polymeric matrix and biocompatible agent is prepared, and the coating solution is applied to the device surface in a one-step coating process. The inventive methods and systems allow for significant flexibility in coating methods, while preferably minimizing the time required for providing the coating to the article. Further, preferred methods can provide significant flexibility in processing parameters, since the coating reagents (including polymeric matrix and biocompatible agent) can be applied in an elegant, precise manner to the device. Thus, preferably, additional processing steps can be optimally eliminated, such as masking, multiple coating steps, purging of coating equipment (such as spray coating equipment), and the like.

In further aspects, the invention provides a method for providing two or more functional surface portions on a medical article, the method comprising steps of: (a) providing a primed first surface portion on the medical article, the primed first surface portion comprising a polymeric initiator; (b) disposing a first composition at the primed first surface portion of the medical article, the first composition comprising a first biocompatible agent including one or more reactive groups, one or more polymerizable groups, or a combination of one or more reactive groups and one or more polymerizable groups; (c) activating the polymerization initiator, reactive groups, or a combination thereof, to form a biocompatible coating layer at the first surface portion; (d) providing a primed second surface portion on the medical article, the primed second surface portion comprising polymerization initiator; (e) disposing a second composition at the primed second surface portion of the medical article, the second composition comprising polymerization initiator including one or more reactive groups, one or more polymerizable groups, or a combination of one or more reactive groups and one or more polymerizable groups; and (f) activating the polymerization initiator, reactive groups, or a combination thereof, to form a biocompatible coating layer at the second surface portion, wherein the first biocompatible agent is different from the second biocompatible agent.

In further aspects, the invention provides a medical article comprising: (a) a first portion that is fabricated of a first device material; and (b) a second portion that is fabricated of a second device material, the second device material being more hydrophobic relative to the first device material, wherein a first biocompatible agent is immobilized at a surface of the first portion via a first biocompatible coating, the first biocompatible coating comprising a polymerization initiator and the first biocompatible agent, the first biocompatible agent including one or more reactive groups, one or more polymerizable groups, or a combination of one or more reactive groups and one or more polymerizable groups, wherein a second biocompatible agent is immobilized at a surface of the second portion via a second biocompatible coating, the second biocompatible coating comprising a nonionic initiator and the second biocompatible agent, the second biocompatible agent including one or more reactive groups, one or more polymerizable groups, or a combination of one or more reactive groups and one or more polymerizable groups, and wherein the first biocompatible agent is different from the second biocompatible agent.

In still further aspects, the invention provides a method of making a medical article comprising steps of: (a) providing a medical article that includes a first portion that is fabricated of a first device material and a second portion that is fabricated of a second device material, the second device material being more hydrophobic relative to the first device material; (b) disposing a first biocompatible coating on a surface of the first portion, the first biocompatible coating comprising polymerization initiator and a first biocompatible agent, the first biocompatible agent including one or more reactive groups, one or more polymerizable groups, or a combination of one or more reactive groups and one or more polymerizable groups; (c) activating the polymerization initiator, reactive groups, or a combination thereof, to form a biocompatible coating layer at the surface of the first portion; (d) disposing a second biocompatible coating on a surface of the second portion, the second biocompatible coating comprising nonionic initiator and a second biocompatible agent, the second biocompatible agent including one or more reactive groups, one or more polymerizable groups, or a combination of one or more reactive groups and one or more polymerizable groups; and (e) activating the polymerization initiator, reactive groups, or a combination thereof, to form a biocompatible coating layer at the surface of the second portion, wherein the first biocompatible agent is different from the second biocompatible agent.

In other aspects, the invention provides a medical article comprising: (a) a body member; (b) a first coating layer along a length of the body member, the first coating layer comprising a hydrophilic polymer; (c) a biocompatible coating in contact with a portion of the first coating layer, the biocompatible coating comprising a biocompatible agent, the biocompatible agent including one or more reactive groups, one or more polymerizable groups, or a combination of one or more reactive groups and one or more polymerizable groups, wherein the biocompatible coating is in contact with a distinct portion of the first coating layer, the distinct portion comprising less than 100% of the first coating layer, and wherein the hydrophilic polymer is selected from poly(vinylpyrrolidone), poly(ethylene glycol), poly(ethylene oxide), poly(ethyloxazoline), poly(propylene oxide), polyacrylamide, poly(vinyl alcohol), and copolymers or combinations of any of these. In some aspects, the first coating layer is in contact with a surface of the body member, and the second coating layer is a top coat on the first coating layer.

Other preferred embodiments of the invention relate to methods for treating patients by providing a medical articles that include more than one biocompatible portion selected to correspond to physiological regions within the patient's body where the implantable device is intended to reside, material portions of the medical article itself, function of the portions of the medical article, and/or bodily fluids with which the portions may come in contact during use. In some aspects, the invention provides methods for treating a patient, the methods including the steps of determining the physiological environments in which a device will reside upon implantation within a patient, determining the biocompatibility functions for each physiological environment identified, selecting biocompatible agents to correspond to each biocompatibility function, and providing the biocompatible agents selected to the corresponding device portions prior to implantation in a patient. In preferred embodiments, the biocompatible agents are non-releasably associated with the device during use (such as residence within the body).

As described herein, an agent is nonreleasably associated with a medical article when the agent is stably incorporated into, or immobilized within, the polymeric matrix material. The result of such immobilization is that, during use of the article, an insignificant amount of the agent is eluted from the polymeric matrix material. The amount of agent eluted from a polymeric matrix material can be determined by comparing the amount of biocompatible agent provided in the polymeric matrix material prior to use (e.g., implantation), with the amount of agent remaining in the polymeric matrix material after use is completed (e.g., subsequent to device removal from a patient). Another method for determining the elution of a biocompatible agent from a polymeric matrix material can involve in vitro washing of a substrate coated with polymeric matrix material and biocompatible agent, followed by determination of the amount of biocompatible agent, if any, that has been released into the wash solution. For example, substrates coated with polymeric matrix material and biocompatible agent can be washed in a detergent (such as, for example, SDS) for an appropriate amount of time (for example, 30 minutes). Suitable wash conditions can be determined by selecting appropriate contact times and agitation rates. After such incubation, the amount of biocompatible agent that has dissociated from the polymeric matrix (and is thus present in the wash) can be determined. Without intending to be bound by a particular theory, it is believed the biocompatible agent is coupled (e.g., covalently) with the polymeric matrix material, thereby immobilizing the biocompatible agent within the polymeric matrix on the device surface. In some instances, the biocompatible agent is believed to be incorporated into the polymeric matrix itself, thereby forming a part of the polymer matrix.

The inventive methods, systems and articles thus provide novel medical articles that, through modification of the article surfaces, provide functional device surfaces. The function of the surface is retained throughout significant term (if not the entire term) of use with a patient. In these aspects, then, the inventive methods, systems and articles can be distinguished from drug eluting devices that are formulated and fabricated to release drug from the device surface, leaving a bare device surface or a drug delivery coating at the surface that does not contain significant drug after a usage period. According to the invention, biocompatible coatings themselves provide a function when contacted with bodily fluids or tissues.

In some aspects, the inventive methods, systems and articles provide biocompatible coatings that retain biocompatible agent activity for extended periods of time when in use. Such activity retention can be due, for example, to the durability of the inventive coatings, incorporation of the biocompatible agent into the polymeric matrix coating at the surface (as opposed to eluting from the surface), the flexibility of the coating methods (e.g., solvent selection, coating conditions, and the like), and surface immobilization itself. For example, when heparin or collagen is utilized as the biocompatible agent, it has been found that sufficient heparin/collagen activity can be retained subsequent to application of the coating to the article surface. This can be advantageous, since incorporation of these (and other similar biocompatible agents) into polymeric coatings can potentially adversely impact or even destroy activity of the biocompatible agent. As discussed herein, the inventive methods and systems allow biocompatible agent to be applied to surfaces via aqueous systems. This can provide a distinct advantage, since use of organic solvents can potentially adversely affect biocompatible agents (for example, by denaturing the biocompatible agent).

In some aspects, the biocompatible agents are modified prior to inclusion in the polymeric matrix material. In other words, such biocompatible agents are non-naturally occurring. Modification of the biocompatible agents can be accomplished, for example, by including reactive groups (such as photoreactive groups) and/or polymerizable groups (such as vinyl groups and the like) in the biocompatible agent. Thus, in some embodiments, it is believed that the photoreactive group of the biocompatible agent can preferentially react with the polymeric matrix material by free radical addition, as opposed to abstracting a hydrogen atom (for example, from the substrate surface). In some aspects, it is believed polymerizable groups of the biocompatible agent (such as collagen or heparin macromers, described herein) can interact with other components of the polymeric matrix in a way that results in the biocompatible agent being incorporated into, and becoming a part of, the polymeric matrix itself. In these aspects, it can be seen that the biocompatible agents form a part of the coating at the surface of the article itself, and are not eluted from the article surface.

In some aspects, the biocompatible coatings not only provide coatings with enhanced durability, but desirable features of the polymeric material (such as lubricious coating features) can be retained, when desired. This can be particularly beneficial when the polymeric matrix material is selected to provide a somewhat lubricious coating. As illustrated in the embodiments shown in the Examples, inclusion of biocompatible agent in an otherwise hydrophilic polymeric matrix did not cause a significant increase in frictional force.

These and other aspects and advantages will now be described in more detail.

BRIEF DESCRIPTION OF THE DRAWINGS

The accompanying drawings, which are incorporated in and constitute a part of this specification, illustrate several aspects of the invention and together with the description of the preferred embodiments, serve to explain the principles of the invention. A brief description of the drawings is as follows:

FIG. 1 is table summarizing friction testing of coatings in accordance with some embodiments of the invention;

DETAILED DESCRIPTION OF THE INVENTION

Figure 2:
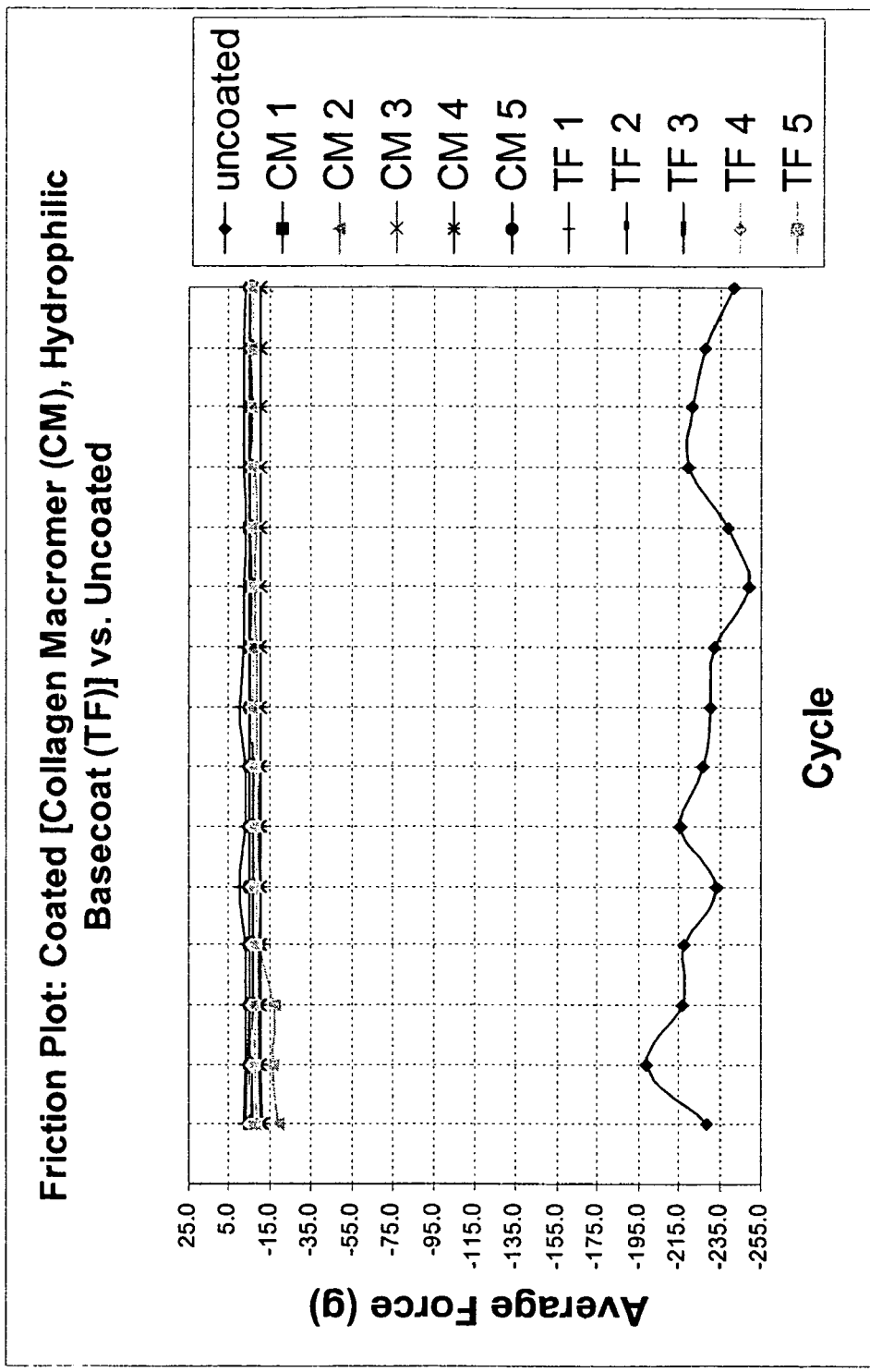
FIG. 2 is a graph illustrating the relationship of average frictional force (g, Y-axis) and cycle number (X-axis) of uncoated medical articles versus medical articles made in accordance with one embodiment of the invention.

The embodiments of the invention described below are not intended to be exhaustive or to limit the invention to the precise forms disclosed in the following detailed description. Rather, the embodiments are chosen and described so that others skilled in the art can appreciate and understand the principles and practices of the invention.

The invention is directed to methods for preparing a multifunctional medical article that includes more than one biocompatible portion. The biocompatible portions can enhance the ability of the medical article to function or exist in contact with biological fluid and/or tissue of a living organism with a net beneficial effect on the living organism. In preferred embodiments, the biocompatible portions can provide one or more advantages, such as increased patient safety, improved device performance, extension of the useable lifetime of the device, and/or reduced occurrence of unwanted events at selected portions of the device, such as adherence of unwanted blood components, blood clotting, and/or cellular debris adherence, and the like.

The inventive polymeric matrices can be used to provide a coating to a wide variety of articles. As used herein, "article" is used in its broadest sense and includes such objects as medical devices. Such articles include implantable devices such as catheters (including sensor catheters, transmyocardial sensor or sensor catheters, and the like that are intended to contact and/or reside within distinct physiological environments of a patient), embolization devices (such as coils), osteochondral fixatives, transdermal access devices or shunts, tunneled access catheters or shunts, implantable devices having sensor components (such as cardiac pacing leads, blood component sensing devices), and the like. Other illustrative articles include implantable devices such as percutaneous cardiac devices (such as heart valves), artificial valves, stented grafts, stented valves, valved grafts, and the like. External medical articles such as blood collection and/or component separation equipment (such as platelet collection and/or cell separation, concentration, or counting systems), hemodialysis or other blood filtration systems and components, blood oxygenation or other blood processing systems and components, other blood diagnostic systems, and the like are also included.

As used herein, the term "biocompatible" generally refers to the ability of an object to be accepted by and to function in contact with a recipient without eliciting an adverse foreign body response (such as, for example, an immune, inflammatory, thrombogenic, or the like response). For example, when used with reference to one or more of the polymeric matrix materials of the invention, biocompatible refers to the ability of the polymeric matrix material (or polymeric matrix materials) to be accepted by and to function in its intended manner in a recipient.

Accordingly, a surface of a medical article can be characterized as "biocompatible" if it is capable of functioning or existing in contact with biological fluid and/or tissue of a living organism with a net beneficial effect on the living organism. This may include a desirable foreign body response that initiates improved tissue healing. Biocompatibility over the intended treatment duration (residence time of the device within the body and/or residence time of the article in contact with bodily fluids) of the medical article is desired for the purpose of reducing disturbance of a host organism. For example, various biocompatible agents such as antithrombogenic agents, anti-restenotic agents, cell attachment proteins, growth factors, and the like, can be provided at the surface of a medical article. For instance, antithrombogenic agents can reduce the generation of substances as part of the clotting cascade, antirestenotic agents can reduce generation of aggressive scar tissue growth around the medical article, while cell attachment proteins can contribute to the growth of a layer of endothelial cells around the medical article.

Several benefits can be provided by biocompatible medical article surfaces. For example, such surfaces can increase patient safety, improve device performance, reduce adherence of blood components, inhibit blood clotting, keep device surfaces free of cellular debris, and/or extend the useable lifetime of the device.

One biocompatible agent that has been utilized to improve biocompatibility of medical device surfaces is heparin. Heparin is a pharmaceutical that has been used clinically for decades as an intravenous anticoagulant to treat inherent clotting disorders and to prevent blood clot formation during surgery and interventional procedures. Heparin molecules are polysaccharides with a unique chemical structure that gives them specific biological activity. When heparin is immobilized onto the surface of a medical device material, it can improve the performance of the material when in contact with blood in several ways: 1) it can provide local catalytic activity to inhibit several enzymes critical to the formation of fibrin (which holds thrombi together); 2) it can reduce the adsorption of blood proteins, many of which lead to undesirable reactions on the device surface; and 3) it can reduce the adhesion and activation of platelets, which are a primary component of thrombus.

In addition to heparin, other biocompatible agents that can be provided on a medical article to improve biocompatibility include extracellular matrix (ECM) proteins or ECM peptides derived from these proteins. Surfaces modified with appropriate proteins or peptides are less likely to be recognized as foreign than the original article surface and will promote the attachment and overgrowth of specific cell types.

In some aspects, the methods and articles described herein are particularly suitable for preparing a multifunctional surface on a medical article that includes distinct biocompatible portions having distinct functions. The presence of more than one biocompatible portion on a single article can render the overall article more suitable for its particular use, especially in the case where the article encounters more than one physiological environment and/or conditions.

Medical articles can include numerous surfaces. Such surfaces may be distinguished by a number of factors, such as, for example, location on the article (for example, interior versus exterior surfaces, or surfaces lying in a single plane versus multidimensional surfaces), structural role within the medical article (for example, components that are assembled to form a single article, or articles including a distal tip, or the like), or functional role within the medical article (movable versus stationary). The present invention provides the ability to provide any number of surfaces, as well as any combination of surfaces, of a selected medical article with a wide variety of biocompatible functions. The biocompatible functions are chosen based upon the physiological environment to which the surfaces of the medical article are exposed during use within a patient. The inventive methods of providing the biocompatible agent to the surfaces allows virtually unlimited ability to customize the surfaces of the medical article based upon such physiological environments. Given the flexibility of the inventive systems and methods, it will be readily apparent that reference to a "surface" in the singular form herein is not limited to a single surface of the medical article, but can include any number and any combination of surfaces of the medical article. Therefore, throughout this description, reference to a "surface" of a medical article is understood to include any one or more surfaces of the article.

In some aspects, the invention is directed to methods and apparatuses for effectively treating an implantation site within a patient's body, and in particular for sites within a patient's body that include more than one physiological environment. Different physiological environments can exist, for example, within the blood stream versus outside the blood stream (intravascular versus extravascular); or within tissue versus outside tissue (including tissues such as epithelial, connective, skeletal, muscular, glandular, nervous tissue); or within an organ versus outside the organ. Given the limitless way in which distinctions could be made between types of tissues, these examples are understood to be illustrative only.

In some embodiments, the inventive medical articles and methods can optionally include a releasable component as well. For example, it can be beneficial, in some applications, to additionally include a therapeutic agent intended to be eluted from the medical article surface during residence within the body. Exemplary therapeutic agents that can find application in connection with the invention include agents that promote fibrosis or promote antithrombotic effect of the medical article. Such therapeutic agents can be adapted to be eluted from the medical article during use, to thereby enhance the effect of the medical article within the body.

In order to be properly introduced and utilized, implantable devices of all sorts of types are preferably designed to accommodate needs for advanceability, manipulability, and crossability to the distal end of the device as such is applied to the proximal end of the device. For purposes of this application, the following terms are given the following meaning. Advanceability is the ability to transmit force from the proximal end of the device to the distal end of the device. The body member of the device should have adequate strength for advanceability and resistance to buckling or kinking. Manipulability is the ability to navigate tortuous vasculature or other body passages to reach the treatment site. A more flexible distal portion is known to improve manipulability. Thus, it can be desirable to provide a device having a body member with some elastomeric properties to improve flexibility in some applications. Crossability is the ability to navigate the device across tissue barriers or narrow restrictions in the body.

Optimization of advanceability, manipulability, and crossability can be accomplished by carefully choosing the device material and its physical characteristics, such as thickness of the material forming the body member. Further, in order to achieve a combination of desired properties at different parts of the device itself, the device can be fabricated to combine a plurality of components together to define a device body member. That is, a portion of the overall length of a body member of the device can comprise a different component than another. These one or more portions can comprise components of different physical characteristics and/or different materials. For example, a distal tip portion can be provided that is more resilient than the remainder of the device body member for better crossability and to provide a softer leading end of the device for abutting body internal membranes and the like. Different materials include different metallic materials or polymeric materials from one another, for example, or similar polymers of different densities, fillers, crosslinking, degradation rates, or other characteristics. In particular, a portion of a device body member can comprise a material chosen for flexibility to allow flexion of the device during residence within the body (for example, in such areas as joints, where movement of the tissues in the area is likely) while another portion can comprise a material chosen for axial and/or torque transmission (to assist in placement of the device).

Exemplary devices that include multiple portions fabricated from multiple materials are physiological sensors. Recent interest has developed in the area of wireless implantable monitoring devices. Such devices can be used to monitor and collect physiological data from conscious, freely moving mammals. An exemplary device can monitor heart function, such as by monitoring left ventricle pressure (LVP). Such device can be inserted into and through heart muscle, with a distal tip portion that resides within the heart chamber during use. Thus, these devices can include a distal portion that is fabricated to cross tissue barriers (such as heart muscle) and provide a sensing and/or monitoring function once in place, an intermediate portion that is fabricated to transverse tissue upon implantation and during residence within a patient, and a more proximal portion that is flexible and durable that is intended to reside in extravascular environment, such as the subcutaneous layers or the interiperitoneal space. Other sensors can monitor physiological parameters such as blood pressure, temperature, biopotentials (such as ECG, EMG, EEG), and physical activity of the patient.

For multi-component medical articles, individual portions of the article can be fabricated from different materials (for example, metal or polymer). Moreover, individual portions of the medical article can provide different functions (for example, monitoring versus transmitting). In addition, individual portions can reside in significantly different physiological environments (for example, blood-contacting versus tissue-transversing). In some aspects, the material properties at the surface of the medical article can be different for the same device. For example, a medical article can be fabricated of two or more different materials, wherein one material is more hydrophobic relative to the other material(s). Hydrophobicity at the article surface can be characterized, for example, by measuring contact angle or spreadability of water at the surface, and/or by determining the critical surface energy of the material by measuring the contact angles of various solvents and known surface tensions upon the material and extrapolating. Materials that tend to be more hydrophobic relative to other materials commonly utilized to fabricate medical devices include, for example, chloro- or fluoro-polymers. Other illustrative polymers that are relatively hydrophobic include polydimethyl siloxane and other siloxane modified polymers, polyethylene and certain other polyolefins, and certain polyurethanes, among others. Exemplary polymeric materials include chloro- and fluoro-saturated polymers, such as PTFE. As discussed elsewhere herein, such relatively hydrophobic materials can be coated, in some embodiments, utilizing a swellable or hydrophilic polymer.

One class of polymers that can be used to fabricate portions of a medical article includes halogenated polymers, for example, chlorinated and/or fluorinated polymers. In some embodiments the substrate material includes a perhalogenated polymer. "Perhalogenated" refers to polymers wherein any carbon-bonded hydrogen is replaced by a halogen atom such as chlorine or fluorine. In some embodiments the substrate material includes a "perfluorinated" polymer, referring to polymers wherein all of the carbon-bonded hydrogens are replaced with fluorine. In some embodiments "partially fluorinated" polymers are used, referring to substrate polymers wherein not all carbon-bonded hydrogens are replaced by fluorine atoms, for example, at least one-fourth of the hydrogen atoms bonded to carbon atoms are replaced with fluorine atoms. A "fluorinated thermoplastic" refers to a fluoropolymer having a distinct melting point, as distinguished from amorphous materials such as fluoroelastomers that usually do not have such a melting point. A "thermoplastic elastomer" refers to a rubber-like material that can be processed like thermoplastic materials.

Fluoroplastics can be useful as substrate materials because of properties they confer, such as chemical resistance properties. However, it is often difficult to covalently bond materials to the surface of substrates constructed from fluoropolymers because fluoropolymer-based substrates have surfaces that are poorly reactive or non-reactive. These fluoropolymers, including those commonly known under the trade name of Teflon™, have very lubricious and hydrophobic surface properties.

Examples of perhalogenated polymers that can be used as substrate materials include perfluoroalkoxy (PFA) polymers, such as Teflon™ and Neoflon™; polychlorotrifluoroethylene (PCTFE); fluorinated ethylene polymers (FEP), such as polymers of tetrafluoroethylene and hexafluoropropylene; poly (tetrafluoroethylene) (PTFE); and expanded poly(tetrafluoroethylene) (ePTFE). These polymers typically have melting temperatures ranging from about 100° C. to about 330° C.

Examples of partially fluorinated polymers include various combinations of interpolymerized units of TFE (tetrafluoroethylene), hexafloropropylene (HFP), vinylidene fluoride (VDF), perfluoro alkyl or alkoxy vinyl ethers, and nonfluorinated olefins. Materials in this class include TFE/HFP/VDF copolymers such as THV (a polymer of tetrafluoroethylene, hexafluoropropylene and vinylidene fluoride), ETFE (a polymer of tetrafluoroethylene and ethylene), HTE (a polymer of hexafluoropropylene, tetrafluoroethylene, and ethylene), polyvinylidene fluoride (PVDF; such as Kynar™, Foraflon™, Solef™, Trovidur™), TFE/P (tetrafluoroethylene/propylene), and ethylene chlorotrifluoroethylene (ECTFE) copolymers, such as Halar™.

Other fluoropolymers are known in the art and described in various references, such as, W. Woebcken, Saechtling International Plastics Handbook for the Technologist, Engineer and User, $3^{rd}$ Ed., (Hanser Publishers, 1995) pp. 234-240.

To illustrate the use of a fluoropolymer as a substrate material to fabricate a portion of a medical article according to the present invention and to demonstrate the advantages that the inventive coatings can provide to these types of substrates, the preparation of a hydrophilic coating including biocompatible agent on the surface of an ePTFE substrate is described. Upon review of the teachings herein, one of skill in the art will readily appreciate the applications to various substrate materials.

Despite the multi-component aspect of such medical articles, it would be particularly beneficial to be able to coat such articles in a minimal number of coating steps, especially when it is desired to provide more than one biocompatible agent in association with surfaces of the medical article. Moreover, it would be beneficial to provide precision coating techniques that allow different biocompatible agents to be associated with distinct portions of the medical article, without adversely impacting the various biocompatible functions to be provided by such distinct portions (such as, for example, such impact resulting from cross-contamination of biocompatible agents of differing portions of the medical article). Further, it would be beneficial to be able to provide such biocompatible characteristics at medical article surfaces without impacting the function of the article. This can be important, for example, when coating a sensing portion of a device. If the coating is too thick or otherwise bulky or inconsistent, the coating can interfere with the sensing ability of the device.

Even further, it would be beneficial to be able to provide such biocompatible characteristics to a multi-component medical article after the various components of the article have been assembled into a unitary medical article. In other words, it would provide significant advantage to be able to coat the final medical article as it is assembled, as opposed to coating individual components that are subsequently assembled to form the complete medical article. By coating the medical article after it has been assembled for implantation, damage to the coating that may occur during assembly of the components may be minimized or avoided.

Preferred inventive medical articles and methods can provide superior biocompatibility for these complex applications in many aspects. In some aspects, the inventive coatings can be applied to a wide variety of medical article materials that can be combined to form a single medical article. The coatings can provide an adherent, durable coating that can be maintained on the selected article material surface during use of the article.

In some aspects, the inventive coatings can be applied in ways that do not interfere with the intended function of the various components of a medical article. The inventive methods allow provision of thin, conformal coatings on the medical article surface. Thin coatings can be particularly useful for small implantable devices. Further, it is readily apparent that for many implantable devices, a coating that is too thick can impede the function of the device. Many conventional coatings can increase the diameter of the device, causing them to stick within a microcatheter lumen as they are being delivered to the implantation site. In contrast, the invention provides multifunctional devices that include a coating that does not significantly increase the dimensions of the device that is being coated. This, in turn, can ensure that the functionality of the device is unlikely to be compromised. The inventive methods allow the provision of thin, conformal, biocompatible coatings on the surface that do not significantly increase the profile of the device. Preferred coatings do not interfere with the device ability to sense the target parameters.

In some aspects, the inventive coatings can be utilized to provide different biocompatible functions to distinct portions of a single medical article, to customize the biocompatible functions to the anticipated physiological environments the medical article will encounter during use.

Additionally, the inventive methods can be used to provide multifunctional coatings on intricate medical article substrates. For example, the invention can be used to provide more than one biocompatible function to porous substrates (such as grafts), combination medical articles (medical articles including multiple configurations), and the like. Moreover, the number of steps required to provide such multifunctional coatings on medical articles can be significantly reduced. In some aspects, the inventive methods can be used to provide coatings having multiple biocompatible agents on a single medical article in a minimal number of coating steps.

According to some aspects of the invention, medical articles have been developed that can be used at any implantation site that includes more than one physiological environment. To facilitate the discussion of the invention, use of the invention in conjunction with a transmyocardial catheter having an intravascular tip will be addressed. Transmyocardial catheters are selected as a result of the particular difficulties encountered when treating the heart with these devices, for example, arising from different portions of the device residing within very different physiological environments. For example, in this particular application, the invention can provide a device having a proximal portion that promotes healing, and a distal portion that promotes blood compatibility (for example, by providing a surface having less cell adhesion, activation, and/or thrombus formation) without affecting monitoring function. Further, in terms of lowering the risk of damage to body tissues while providing a superior device, the advantages of this implantable device can be clearly presented. However, it is understood that the articles and methods disclosed are applicable to any treatment needs, for example, treatment of regions of the body that include more than one distinct physiological environment, such as, for example, catheters intended to encounter blood and tissue environments, devices inserted through the skin and intended to reside transcutaneously (such that healing functions at the skin surface may be desirable), various sensor catheters, prosthetic heart valves, osteochondral fixatives (where both bone growth and cartilage healing can be desirable) and the like devices that encounter and/or reside within more than one physiological milieu during use, as well as external medical articles that come in contact with bodily fluids (such as blood separation devices and the like).

In another illustrative embodiment, a biocompatible heart valve can be provided in accordance with principles of the invention. It can be desirable to provide different biocompatible functions at different portions of the valve. For example, it can be desirable to provide an increased resistance to calcification and/or increased resistance to thrombus formation at some portions (such as the valve leaflets), while promoting integration of tissue into the sewing cuff, stent, or other member designed to fix the device within the tissue.

In other aspects, the invention can be utilized to provide medical articles that include gradients of biocompatible functions along the surface of a single medical article. One illustrative embodiment of these aspects is an implantable device that include a distal protection device. One such implantable device can include a basket at the distal portion of the device. These types of devices typically include a sharp tip that is fabricated to cross a lesion within the body, a distal protection device at a distal region of the device, and a portion that extends from the distal region to a more proximal region. It can be desirable to provide biocompatible agents such as lysine, heparin, or the like, at a distal portion of the device, particularly the distal protection device. Such biocompatible agents can provide antithrombotic effects to the selected portion of the device, and thereby improve the biocompatibility of the device. For the same device, it can also be desirable to provide a gradient of lubricity along the portion of the device that extends from the distal region to the proximal region. In one such embodiment, for example, the most distal region can be provided with a more lubricious surface functionality, to enhance the ability of this portion of the device to easily maneuver within the body. At the most proximal region of the device, however, it can be desirable to provide a more tactile feel, so that the surgeon utilizing the device can obtain some purchase of the device surface in selected proximal portions of the device. Along the device, in the region spanning between the selected distal region and the selected proximal region, it can be desirable to provide a gradient of lubricity, wherein the lubricity gradually changes from a more lubricious surface to a more tactile surface (from distal to proximal).

Gradients of selected biocompatible functions can be easily provided to a single medical article in accordance with the inventive methods and systems. The components of the coatings described herein, as well as the flexibility in formulating and applying these components to a medical article surface, provide an elegant system for creating a wide range of biocompatible features for a single medical article. Thus, when it is desirable to provide a gradient of a particular biocompatible function, the amount of the biocompatible agent (or agents, as the case may be) within the coating composition can be manipulated along the surface of the medical article. Similarly, the particular biocompatible agents included within the coating composition can be manipulated along the surface of the medical article to thereby provide a gradient of biocompatible function along the length.

Generally speaking, the invention provides medical articles wherein different portions of the article include different biocompatible agents that encounter different physiological environments and/or bodily fluids during use.

According to the invention, more than one biocompatible portion is provided in association with a single medical article. The biocompatible portions are provided at one or more surfaces of the medical article. The surface can be one or more surfaces of medical articles intended to function in contact with tissue and/or fluids of living organisms. Typically, the selected surfaces of the medical article will encounter distinct physiological environments upon implantation and use of the medical article.

In its article aspect, the invention provides medical articles that include more than one biocompatible portion, each biocompatible portion comprising a polymeric matrix including a biocompatible agent. The biocompatible agent is incorporated into and forms a part of the polymeric matrix. These aspects will now be described in more detail.

The invention provides medical articles that are useful for treating regions of the body having distinct physiological environments and/or that can come into contact with different bodily fluids during use. At least a portion of the medical article includes a matrix material. Suitable matrix materials are described, for example, in U.S. Pat. No. 6,007,833 (Chudzik et al., Crosslinkable Macromers Bearing Initiator Groups), U.S. Pat. No. 6,156,345 (Chudzik et al., Crosslinkable Macromers Bearing Initiator Groups), and U.S. Pat. No. 6,410,044 (Chudzik et al., Crosslinkable Macromers), and U.S. Publication No. 2003/0031697 (Chudzik et al., Crosslinkable Macromers).

In one embodiment, the matrix material is provided by a crosslinkable macromer system that includes a polymeric backbone, polymerizable groups, and initiator groups. As used herein, a macromer is a polymer that is capable of undergoing further polymerization. Generally speaking, the crosslinkable macromer system comprises two or more polymer-pendent polymerizable groups and one or more initiator groups. The initiator group(s) can be polymer-pendent or free (not associated with a polymer). For purposes of discussion, reference will be made to the singular form when referring to the initiator group. However, it will be understood that one or more initiator groups can be used in accordance with the inventive concepts, and use of the singular form of the term will not be limited to inclusion of one initiator group. When the initiator is in the form of a polymeric initiator, the polymerizable groups and the initiator group can, in some embodiments, be pendent on the same polymeric backbone. In other embodiments, the polymerizable groups and initiator group are pendent on different polymeric backbones. In yet further embodiments, the initiator group is provided as free (non-polymer bound) initiator molecules.

The polymeric backbone can be synthetic or naturally occurring, and includes a number of macromers previously described as useful for the preparation of polymeric matrices. Generally, the polymeric backbone is soluble, or nearly soluble, in aqueous solutions such as water, or water with added organic solvent (for example, dimethylsulfoxide), or can be rendered soluble using an appropriate solvent or combination of solvents. In some embodiments, the polymeric backbone is a material that is a liquid under ambient physiological conditions. Backbones for use in preparing biodegradable gels are preferably hydrolyzable under in vivo conditions.

In general, polymeric backbones suitable for use in accordance with the invention can be described as falling within one of two categories: biodegradable (or bioresorbable), and biostable reagents. These can be further categorized as reagents that form hydrophilic, hydrogel matrices versus reagents that form non-hydrogel matrices. Each type will be described.

Biodegradable hydrogel-forming backbones are generally naturally occurring polymers such as polysaccharides, examples of which include, but are not limited to, hyaluronic acid (HA), starch, dextran, heparin, chondroitin sulfate, dermatan sulfate, heparan sulfate, keratan sulfate, dextran sulfate, pentosan polysulfate, and chitosan; and proteins (and other polyamino acids), examples of which include but are not limited to gelatin, collagen, fibronectin, laminin, albumin, elastin, and active peptide domains of these. Matrices formed from these materials degrade under physiological conditions, generally via enzyme-mediated hydrolysis.

Hyaluronic acid, when derivatized with polymerizable groups in the manner described herein, can provide a variety of advantages. According to the invention, hyaluronic acid, as well as other polysaccharides and polyamino acids (such as collagen) can be effectively derivatized in organic, polar, anhydrous solvents and solvent combinations. One exemplary solvent is formamide, and combinations of solvents therewith. Functionally, the solvent or solvent system is one in which the polymer is sufficiently soluble and that permits its derivatization to the desired extent, while minimizing phenomena that adversely affect the biological activity of the polymer (if any), such as denaturation of collagen that adversely affects desirable cell binding.

For example, hyaluronic acid can be reacted in formamide (and TEA, for pH control) with a reactive moiety in the form of glycidyl acrylate in order to derivatize the hyaluronic acid molecules with acrylate groups. The number and/or density of acrylate groups can be controlled using the inventive methods, for example, by controlling the relative concentration of reactive moiety to saccharide group content.

Biodegradable matrix-forming backbones are generally synthetic polymers prepared via condensation polymerization of one or more monomers. Matrix-forming polymers of this type include polylactide (PLA), polyglycolide (PGA), polycaprolactone (PCL), as well as copolymers of these materials, polyanhydrides, and polyortho esters.

Biostable hydrogel matrix-forming backbones are generally synthetic or naturally occurring polymers that are soluble in water, matrices of which are hydrogels or water-containing gels. Examples of this type of backbone include polyvinylpyrrolidone (PVP), polyethylene glycol (PEG), polyacrylamide (PAA), polyvinyl alcohol (PVA), and the like. As discussed herein, these polyemrs can provide hydrophilic properties as well.

Biostable matrix-forming backbones are generally synthetic polymers formed from hydrophobic monomers such as methyl methacrylate, butyl methacrylate, dimethyl siloxanes, and the like. These backbone materials generally do not possess significant water solubility but can be formulated as neat liquids that form strong matrices upon activation. It is also possible to synthesize backbone polymers that contain both hydrophilic and hydrophobic monomers.

Polymeric backbones in accordance with the invention can optionally provide a number of desirable functions or attributes. For example, polymeric backbones can be provided with water soluble regions, biodegradable regions, hydrophobic regions, as well as polymerizable regions.

The inventive macromer systems include two or more polymerizable groups. As used herein, the term "polymerizable group" generally refers to a group that is capable of propagating free radical polymerization, such as carbon-carbon double bonds. Preferred polymerizable groups include vinyl or acrylate groups. Exemplary polymerizable groups include acrylate groups, methacrylate groups, ethacrylate groups, 2-phenyl acrylate groups, itaconate groups, acrylamide groups, methacrylamide groups, and styrene groups.

See, for example, U.S. Patent Publication No. US-2004-0202774-A1 (Chudzik et. al., "Charged Initiator Polymers And Methods Of Use," published Oct. 14, 2004).

Typically, polymerizable groups are incorporated into a macromer subsequent to the initial macromer formation using standard thermochemical reactions. For example, polymerizable groups can be added to collagen via reaction of amine-containing lysine residues with acryloyl chloride or glycidyl acrylate. These reactions result in collagen containing pendent polymerizable moieties. Other methods of prepared collagen macromers are described herein as well. Similarly, when synthesizing a macromer for use as described in the present invention, monomers containing reactive groups can be incorporated into the synthetic scheme. For example, hydroxyethylmethacrylate (HEMA) or aminopropylmethacrylamide (APMA) can be copolymerized with N-vinylpyrrolidone or acrylamide yielding a water-soluble polymer with pendent hydroxyl or amine groups. These pendent groups can subsequently be reacted with acryloyl chloride or glycidyl acrylate to form water-soluble polymers with pendent polymerizable groups.

One preferred macromer including polymerizable groups comprises a PEG backbone having polymerizable acrylate groups, particularly a PEG backbone having more than two polymerizable groups, more particularly preferred is PEG-triacrylate. One exemplary method of preparing a PEG backbone having multiple acrylate groups is described in more detail in the Examples.

The macromer system further includes one or more initiator groups. In some aspects of this embodiment, the macromer system can comprise a polymeric backbone having both the polymerizable groups and initiator group covalently bound thereto. Pendent initiator groups can be provided by bonding the initiator groups to the backbone at any suitable time, for example, prior to the formation of the macromer (for instance, to monomers used to prepare the macromer), or to the fully formed macromer itself. The macromer system itself will typically comprise a small percentage of macromers bearing both initiator groups and polymerizable groups. The majority of macromers will provide only pendent polymerizable groups, since the initiator groups are typically sufficient if present at far less than 1:1 stoichiometric ratio with macromer molecules.

In other aspects, the macromer system can comprise polymerizable macromers and polymeric initiator as a separate component. In other words, the polymerizable macromers do not include a pendent initiator group, but the initiator group is provided as a distinct component to the system comprising a polymeric backbone heaving initiator groups bound thereto.

In either of the above aspects (initiator bound to polymeric backbone or initiator as a separate component), the initiator will be referred to herein as a "polymeric initiator," by virtue of the attachment of such initiator groups to a polymeric backbone in practice of the inventive concepts. Macromer systems that include polymeric initiator can be desirable when solubility of the initiator is a concern. Solubility, for instance, can be improved by virtue of the ability to control the aqueous or organic solubility of the polymeric initiator by controlling the backbone. In some instances, the polymeric initiator can also provide reduced toxicity, since the polymeric initiators of the invention typically cannot diffuse into cells in the course of immobilization.

Initiator groups useful in the inventive systems include those that can be used to initiate, by free radical generation, polymerization of the macromers to a desired extent and within a desired time frame. In some embodiments, the polymeric initiators are photosensitive molecules that capture light energy and initiate polymerization of the macromers. Crosslinking and polymerization are generally initiated among macromers by a light-activated free-radical polymerization initiator. Suitable long wave ultraviolet (LWUV) light-activatable molecules include, for example, 4-benzoylbenzoic acid, [9-oxo-2-thioxanthanyl)-oxy]acetic acid, 2-hydroxy thioxanthone, and vinyloxymethylbenzoin methyl ether. Suitable visible light activatable molecules include ethyl eosin, acetophenone derivatives (such as 2,2-dimethoxy-2-phenyl acetophenone), thioxanthone, benzophenone, and camphorquinone.

Other suitable polymeric initiators are thermosensitive molecules that capture thermal energy and initiate polymerization of the macromers. Suitable thermally activatable molecules include 4,4' azobis(4-cyanopentanoic) acid; 2,2-azobis[2-(2-imidazon-2-yl)propane]dihydrochloride; and benzoyl peroxide.

Photoinitiation of the free radical polymerization of macromers of the invention will generally occur by one of three mechanisms. The first mechanism involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether, acetophenone, and the like.

The second mechanism involves a hydrogen abstraction reaction, either intra- or intermolecular. This initiation system can be used without additional energy transfer acceptor molecules and utilizing nonspecific hydrogen abstraction, but is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone, thioxanthone, camphorquinone, and the like. When using a polymeric initiator of the hydrogen abstraction variety, pendent tertiary amine groups can be incorporated into the polymeric backbone of the macromer, thereby promoting formation of polymer-bound free radicals.

The third mechanism involves photosensitization reactions utilizing photoreducible or photo-oxidizable dyes. In most instances, photoreducible dyes are used in conjunction with a reductant, typically a tertiary amine. The reductant intercepts the induced triplet producing the radical anion of the dye and the radical cation of the reductant. Examples of molecules exhibiting photosensitization reactivity and useful in a polymeric initiating system include eosin Y, rose bengal, erythrosin, and the like. Reductants can be incorporated into the polymer backbone, thereby promoting formation of polymer-bound free radicals.

One beneficial effect of the use of polymeric initiators to polymerize macromers is the increased efficiency of polymerization exhibited by these polymeric initiators as compared to their low molecular weight counterparts. This increased efficiency can be seen in all three photoinitiation mechanisms useful for the polymerization of macromers. Generally speaking, when forming polymeric matrices in the presence of biologic or bioactive materials, it is desirable to minimize the exposure time of the material to the energy source used to initiate polymerization. Thus, high efficiency of initiation can be preferred.

Moreover, when matrix strength or durability is important for a particular application, high efficiency of initiation can be desirable. When a matrix-forming system is initiated, the free radical polymerization of the system is propagated until gelation and vitrification of the polymerizing system render the diffusion of the elements of the matrix-forming system too difficult. Therefore, the higher the efficiency of the initiation system, the more complete the polymerization resulting in the formation of stronger, more durable matrices. The polymeric initiation systems, in accordance with the inventive systems, can in some embodiments provide a higher degree of efficiency, without the use of accelerants, than is attainable using nonpolymer-bound, low molecular weight initiators.

Another beneficial effect can be realized when the initiating groups on the polymeric initiators consist of groups exhibiting hydrogen abstraction reactivity (the ability to abstract hydrogens intermolecularly). This beneficial effect can be important when macromer systems containing these initiators are used in applications involving the "adhesion" of the matrix to one or more surfaces. Since initiators exhibiting this type of reactivity can abstract hydrogen atoms from adjacent molecules, when a macromer system containing polymeric initiators of this type is applied to a substrate, photoactivation of the system can cause the abstraction of hydrogen atoms from the substrate by the initiators, thus forming a free radical on the substrate and a free radical on the initiator. This diradical can subsequently collapse forming a covalent bond between the macromer system and the substrate.

Other initiator groups on the same macromer can initiate free radical reactions with other macromers resulting in the formation of a crosslinked matrix covalently bound to the surface. Initiator groups exhibiting this type of reactivity include analogs of benzophenone, thioxanthone, and the like.

Optionally, the use of initiators for initiating radical chain polymerization, can include the addition of one or more monomeric polymerization accelerants to the polymerization mixture, the accelerants serving to enhance the efficiency of polymerization. Polymerization accelerants useful in the invention are typically monomers, which improve the reactivity of the macromer systems. Polymerization accelerants that have found particular utility for this application include N-vinyl compounds, particularly N-vinyl pyrrolidone and N-vinyl caprolactam. Such accelerants can be used, for instance, at a concentration in the range of about 0.01% to about 5%, or about 0.05% to about 0.5% by weight, based upon the volume of the macromer system.

In other embodiments, the polymeric initiator can comprise a polymeric backbone with pendent initiator groups and pendent affinity groups. These affinity groups enable the polymeric initiator to bind to target groups on surfaces of interest, thereby allowing the polymeric initiator to bind to the surface of interest. In this manner, interfacial polymerization of macromers can be accomplished. A solution of polymeric initiator containing pendent affinity groups is applied to a surface with target sites. The affinity groups on the polymeric initiator react with the sites on the surface causing the polymeric initiator to bind to the surface. Excess polymeric initiator can then be washed away, if desired. A solution of a polymerizable macromer is then applied to the surface. When light energy is applied to the system, a free radical polymerization reaction is initiated only at the surface of interest. By varying the concentration of the polymerizable macromer and the illumination time, the thickness and crosslink density of the resulting matrix on the surface can be manipulated.

Suitable affinity groups include chemical entities having an affinity for target groups present on surfaces of interest. Such affinity groups are capable of associating (for example, bonding) to target groups on surfaces of interest. Exemplary affinity groups include charged groups, such as positively charged groups. The interaction between the affinity groups and target groups is typically relatively nonspecific, for example, based upon electrostatic or hydrophobic interaction. Suitable charged groups can include ternary and quaternary cationic groups, such as quaternary ammonium, quaternary phosphonium, ternary sulfonium, and the like. These groups can be provided in, for example, alkylated or alkoxylated forms having, for example, in the range of 1-6 carbons on each chain. Examples include, but are not limited to tetraalkylammonium, tetraalkoxyammonium, trialkylsulfonium, trialkoxysulfonium, tetraalkylphosphonium, and tetraalkoxyphosphonium cations. Specific examples include tetramethylammonium, tetrapropylammonium, tetrabenzylammonium, and the like.

The affinity groups can be spaced in a random or ordered pattern along the length of the polymer backbone or can be present primarily on one end of the polymer backbone if desired. The polymeric initiator can also include different combinations of affinity groups, if desired.

In other embodiments, if desired, the surface of the medical article can be modified prior to application of a polymeric matrix material, to provide target groups at the article surface that are capable of associating with the affinity groups provided by the polymeric initiator. For example, the surface can be modified to provide a net charge, and electrostatic attraction can be used to bring the polymeric initiator having a net opposite charge into proximity to the article surface, where polymerization initiation can take place. Other target groups are known and can be utilized in accordance with the general teachings herein. Also, it is understood that many methods described herein do not require any surface pretreatment.

Generally, there are at least two methods by which an initiator group can be incorporated into a polymeric backbone. The first method involves the formation of a monomer that includes the initiator. This can be accomplished readily using standard chemical reactions. For example, the acid chloride analog of an initiator can be reacted with an amine-containing monomer, to form a monomer that contains the initiator. Other methods are known and will not be described further herein.

A second general method of incorporating initiator groups into a polymeric backbone involves coupling a reactive analog of the initiator with a preformed polymer. For example, an acid chloride analog of an initiator can be reacted with a polymer containing pendent amine groups forming a polymer bearing pendent initiator groups. Other known methods can be utilized in accordance with the invention and will not be described further herein.

Although polymeric initiators are suitable as described herein, in some embodiments it can be desirable to utilize a nonpolymeric initiator (one that is not associated with a polymer backbone but is instead "free" of a polymer). Exemplary nonpolymeric initiators are described, for example, in U.S. Pat. Nos. 5,414,075 and 5,637,460 (Swan et al., "Restrained Multifunctional Reagent for Surface Modification"). These patents describe coating reagents that include a chemical backbone having attached to it one or more first photoreactive groups capable of attaching to a surface, and one or more second photoreactive groups capable of initiating free radical polymerization. Optionally, the coating reagents further include spacers that couple the latent reactive groups with the chemical backbone. Chemically, the first and second photoreactive groups, and respective spacers, can be the same or different.

Preferably, the photoreactive groups of the coating reagent according to these embodiments are adapted to undergo reversible photolytic homolysis, thereby permitting photoreactive groups that are not consumed in attachment to the support surface to revert to an inactive, or "latent" state. These photoreactive groups can be subsequently activated, in order to serve as photoinitiator groups for initiating free radical polymerization. Thus, excitation of the photoinitiator is reversible and the group can return to a ground state energy level upon removal of the energy source. In some embodiments, preferred photoinitiators are those groups that can be subject to multiple activation and hence provide increased coating efficiency.

In situations in which all photoreactive groups and spacers are chemically, or at least functionally, the same, the distinction between first and second photoreactive groups can actually be accomplished at the time of the first activation step; that is, those groups that are activated and attach to the surface will be considered "first" photoreactive groups, and those that remain unreacted (whether or not they have been activated) will be considered "second" photoreactive groups.

In some embodiments, the first and second photoreactive groups are coupled to the chemical backbone by spacer chains in such a manner that, upon activation of the photoreactive groups in the presence of a support surface, the first photoreactive groups are capable of covalently bonding to the surface. The second photoreactive groups are thereby conformationally restricted, thus preventing reaction with their spacers, other restricted reagents of the same type, and/or the support surface. In addition, after the first activation step and removal of the activating stimulus (for example, an illumination source), the second photoreactive groups are capable of reverting to their inactivate state and can thereafter be activated (or reactivated, as the case may be) to initiate free radical polymerization.

One exemplary type of spacer is dimethyleneoxy. Thus, in some aspects, the coating reagent can include a chemical backbone having four dimethyleneoxy groups ($-CH_2-O-CH_2$) bonded as spacers to a central tetrahedral carbon atom. The backbone, spacers, and photoreactive groups are described herein, for the sake of simplicity, as being distinct portions of the reagent. In the chemical synthesis of a coating reagent, however, these portions will not typically be provided as three independent precursors. Instead, and most often, the portion referred to as the spacer will be formed as the result of the reaction between two molecules, one that contains the chemical backbone and another that contains the photoreactive group.

Spacers useful in the coating reagent of these embodiments can be coupled to the chemical backbone and can be of any suitable length and structure. A "spacer" as used herein refers to that region of a coating reagent between a photoreactive group and a chemical backbone. Functionally, it is preferred that a spacer does not have any groups or atoms that would be physically accessible to, and/or chemically reactive with, an activated photoreactive group (whether from the same or another reagent molecule), to an extent that would render the coating reagent useless for its intended purpose. At the very least, the spacer should have no atom or groups that would kinetically compete with the binding of photoreactive groups to their intended target, be it a surface or a biocompatible agent. For instance, preferred spacers should typically not include accessible abstractable hydrogen atoms; that is, hydrogen atoms that are accessible to and reactive with the activated photoreactive group of choice.

Molecular modeling techniques, as are available to and within the skill of those in the art, can be used to determine the optimal length and structure of spacers needed to keep photoreactive groups conformationally restricted from reacting. Typically the spacer will have no linear region longer than about 5 atoms (6 bonds), and preferably 4 atoms (5 bonds) in length. Although it is not required that the spacers within a particular reagent be chemically identical, the use of different spacers in a single coating reagent molecule is not generally preferred, since such an embodiment will typically require more synthetic steps and may require more complex chemical separations in their preparation.

Constituent atoms of the spacers need not be aligned linearly. For example, aromatic rings, which lack abstractable hydrogen atoms can be included as part of spacer design in those reagents where the photoreactive group functions by initiating covalent bond formation via hydrogen atom abstraction. In its precursor form (prior to attachment of a photoreactive group), a spacer can be terminated with any suitable functionality, such as hydroxy, amino, carboxyl, and/or sulfhydryl groups, which is suitable for use in attaching a photoreactive group by a suitable chemical reaction, such as conventional coupling chemistry.

The chemical backbone of the coating reagents according to these embodiments refers to the atom, or other molecular structure, to which either the latent reactive groups or spacers are coupled, and which provides, at least in part, the desired steric and conformational restrictiveness between groups or spacers that are attached to the same chemical backbone. The term "core molecule" refers to the combination of chemical backbone and any attached spacers (that is, without photoreactive groups).

The chemical backbone can thus be provided by a single atom, such as a carbon, silicon, nitrogen, phosphorus, or other atom with four or more bonds nonplanar with respect to one another. Alternatively, the chemical backbone can include any suitable chemical (organic and/or inorganic) backbone structure. In some embodiments, the chemical backbone can include molecules having conformationally restricted ring structures (such as inositol, or hexahydroxy cyclohexane) that can be derivatized with latent reactive groups in a manner analogous to that described herein for pentaerythritol, to provide latent reactive groups in both axial and equatorial positions. Other polyhydroxylated compounds such as mono- and disaccharides, and cyclodextrins, are suitable as well, in that they offer alternative opportunities to create other multisubstituted reagents having varying placements and densities of latent reactive groups.

The coating reagent according to these embodiments can be prepared according to conventional synthetic methods. One illustrative reagent can be prepared according to the following protocol: a mixture of the chemical backbone molecule (such as pentaerythritol) and an excess of a derivative of the photoreactive group (such as 4-bromomethylbenzophenone) are dissolved in a suitable solvent and refluxed in the presence of a base capable of alkoxide anion generation. The product, a tetrakis(4-benzoylbenzyl ether) of pentaerythritol can then be purified by preparative chromatography.

Any suitable coupling chemistry can be used to attach the photoreactive group to the core molecule. For example, an ester coupling group can be prepared by reaction of 4-benzoylbenzoyl chloride with pentaerythritol, using a suitable solvent and acid scavenger. Similarly, a urethane coupling group can be generated by reaction of 4-benzophenone isocyanate with pentaerythritol. Also, where the core molecule contains spacers terminated with amine functional groups, as opposed for instance to hydroxyl groups, a photoreactive group can be introduced via an amide functionality, using an acid chloride or an N-oxysuccinimide ester.

Likewise, if the core molecule spacers are terminated with sulfhydryl groups, a maleimide-substituted photoreactive group can be used in the coupling reaction. The coupling reaction of the core molecule (such as pentaerythritol) with the photoreactive group can be preceded by the synthesis of a core molecule that includes not only the pentaerythritol precursor but also spacer extensions based upon molecules that are nonreactive or sterically hindered with respect to reaction with the photoreactive group. Preparation of some exemplary nonpolymeric initiators according to these aspects of the invention is described in more detail in the examples.

Other exemplary nonpolymeric initiators are described, for example, in U.S. Pat. Nos. 6,669,994, 6,278,018, 6,603,040, and U.S. Publication No. US 2004/0137164 A1 (Swan et al., "Water-Soluble Coating Agents Bearing Initiator Groups"). These patents describe coating agents that include one or more charged groups (such as salts of sulfonic, carboxylic, and phosphoric acids) and two or more photoreactive groups, wherein the photoreactive groups are provided as discrete photoreactive groups. Generally speaking, the coating agents described in these commonly owned patents and published applications (as well as any other related application and/or patent) are suitable for use as nonpolymeric initiators in the presently described invention. In accordance with these embodiments, the photoreactive groups comprise one or more first photoreactive groups adapted to attach the coating agent to a surface, and one or more second photoreactive groups adapted to initiate photopolymerization. The coating agents utilize photoreactive groups capable of serving as a photoinitiator to initiate polymerization. The photoinitiator groups are adapted to regeneratively participate in the polymerization process. Preferably, the photoreactive groups are adapted to undergo reversible photolytic homolysis, thereby permitting photoreactive groups that are not consumed in attachment to the support surface to revert to an inactive, or "latent" state. These photoreactive groups can be subsequently activated, in order to serve as photoinitiator groups for initiating free radical polymerization. Thus, excitation of the photoinitiator is reversible and the group can return to a ground state energy level upon removal of the energy source. In some embodiments, preferred photoinitiators are those groups that can be subject to multiple activation in aqueous systems and hence provide increased coating efficiency.

In one aspect, the coating agent can comprise a nonpolymeric core molecule having attached thereto, either directly or indirectly, one or more substituents comprising negatively charged groups, and two or more photoreactive groups, wherein the photoreactive groups are provided as discrete photoreactive groups.

Suitable core molecules comprise nonpolymeric radicals having a low molecular weight (such as molecules having an average molecular weight in the range of about 100 to about 1000 MW). Optionally, core molecules can be provided with water soluble regions, biodegradable regions, hydrophobic regions, as well as polymerizable regions. Examples of suitable core molecules include cyclic hydrocarbons, such as benzene and derivatives thereof.

Any of the photoreactive groups described herein can be utilized as a photoreactive group in accordance with the nonpolymeric initiator embodiments. Photoinitiator groups useful according to these embodiments include those that can be used to initiate photopolymerization of polymerizable groups, by a process of free radical generation, to a desired extent and within a desired time frame. Photoinitiators are responsible for producing initiating species by the action of light energy. Free radicals can be produced by intramolecular photocleavage or hydrogen abstraction (inter- or intramolecular). Exemplary photoinitiators include photoreactive groups described herein. The photoinitiator group (the second photoreactive group) can be the same or different from, the first photoreactive group used to couple the coating agent to a support surface. In some embodiments, the first and second photoreactive groups are adapted to be independently activated by light of different wavelengths (for example, ultraviolet light versus visible light).

The charged group of the nonpolymeric initiator generally refers to a group that is present in ionic form in solution (that is, carries an electrical charged under the conditions (such as pH) of use). Exemplary charged groups include salts of organic acids (such as sulfonate, phosphonate, and carboxylate groups), as well as combinations thereof. One preferred charged group for use in preparing coating agents is a sulfonic acid salt, for example, derivatives of $SO_3^-$ in which the counterion is provided by any suitable positively charged species, such as a potassium or sodium ion, or the like.

Optionally, the coating agent can include spacers between the nonpolymeric core molecule and one or more of the photoreactive groups. A spacer can be provided in situations when it is desired to provide more distance between the photoreactive groups and the core molecule. For example, it can be desirable to provide a spacer to avoid steric hindrance that can result between the core molecule and the photoreactive species, thus inhibiting the photoreactive species from forming covalent bonds with a medical article surface, or from serving as a photoinitiator for polymerization, as the case may be.

In one embodiment, the coating agent comprises a conjugated cyclic diketone having attached thereto, either directly or indirectly, one or more substituents comprising negatively charged groups, and wherein each ketone group of the diketone is adapted to serve as a photoreactive moiety capable of being activated in order to provide a free radical. Preferably, the conjugated cyclic diketone is a quinone selected from substituted and unsubstituted benzoquinone, camphorquinone, naphthoquinone, and anthraquinone.

Illustrative coating agents include anthraquinone sulfonic acid salt, camphorquinone sulfonic acid, hydroquinone monosulfonic acid derivatives, 2,5-bis(4-benzoylphenylmethyleneoxy)benzene-1,4-disulfonic acid dipotassium salt (DBHQ), 4,5-bis(4-benzoylphenylmethyleneoxy)benzene-1,3-disulfonic acid dipotassium salt (DBDS), and 2,5-bis(4-benzoylphenylmethyleneoxy)benzene-1-sulfonic acid mono (or di-) sodium salt. Methods of synthesizing suitable coating agents are described, for example, in U.S. Pat. No. 6,669,994 and U.S. Publication No. US 2004/0137164 A1.

Other exemplary nonpolymeric initiators are described, for example, in U.S. Pat. Nos. 5,714,360 and 6,077,698 (Swan et al., "Photoactivatable Water Soluble Cross-Linking Agents Containing an Onium Group" and "Photoactivatable Cross-Linking Agents Containing Charged Groups for Water Solubility"). These patents describe chemical linking agents that are formed of a di- or higher functional photoactivatable compound having at least one group that is charged under the conditions of use in order to provide improved water solubility. The agents contain two or more photoreactive groups in order to allow the agent to be used as a cross-linking agent in aqueous systems. The linking agents can have the general formula: X—Y—X, wherein each X, independently, is a radical containing a photoreactive group and Y is a radical containing, inter alia, one or more charged groups. In such embodiments, the number and/or type of charged group(s) is sufficient to provide the molecule with sufficient aqueous solubility to allow the agent to be used in a solvent system having water as a major component.

According to these embodiments, the charged group (Y) is a group that is present in ionic form, i.e., that carries an electrical charge under the conditions (such as pH) of use. The charged groups can be nonpolymeric. The type and number of charged groups are sufficient to provide the agent with water solubility (water at room temperature ad optimal pH) of at least about 0.1 mg/ml, or at least about 0.5 mg/ml, or at least about 1 mg/ml. Illustrative charged groups include, but are not limited to, salts of organic acids (such as sulfonate, phosphonate, and carboxylate groups), onium compounds (such as quaternary ammonium, sulfonium, and phosphonium groups), and protonated amines, as well as combinations of any of these.

The photoreactive group (X) can be any of the photoreactive groups described herein.

The macromer systems can be applied to the medical article in any suitable manner, including spraying, dipping, injecting, and/or brushing the macromer system onto the medical article.

In some aspects, preferred nonpolymeric initiator compounds are tetrakis(4-benzoylbenzyl ether) of pentaerythritol ["tetra-BBE-PET"]; tetrakis(4-bezoylbenzoate ester) of pentaerythritol ("tetra-BBA-PET"); 4,5-bis(4-benzoylphenylmethyleneoxy)benzene-1,3-disulfonic acid disodium salt ("DBDS"); and ethylenebis(4-benzoylbenzyldiemthlammonium) dibromide.

According to the invention, the multifunctional medical article includes more than one biocompatible portion, wherein each biocompatible portion comprises a polymeric matrix including a selected biocompatible agent. The biocompatible agents are modified to include reactive groups, polymerizable groups, or a combination of reactive groups and polymerizable groups. In some aspects, the biocompatible agent includes one or more reactive groups for associating the biocompatible agent with the polymeric matrix. In some embodiments, the biocompatible agent includes one or more polymerizable groups. Optionally, polymerization initiator can be provided to the system in addition to the above-described components.

In some aspects, the invention provides methods for preparing a multifunctional medical article having more than one biocompatible portion wherein each biocompatible portion comprises a distinct biocompatible agent. In some aspects, biocompatible agents can be selected to improve the biocompatibility by reducing interaction between the medical article surface and the surrounding environment (for example, with blood and/or surrounding tissues). For instance, the biocompatible agent, when associated with a portion of a medical article surface, can serve to shield the blood from the underlying medical article material. Suitable biocompatible agents for such use preferably reduce the likelihood for blood components to adhere to the medical article and activate, thus reducing the formation of thrombus or emboli (blood clots that release and travel downstream). In some aspects, biocompatible agents can be selected and applied to distinct portions of a medical article surface to improve biocompatibility by assisting in maintaining the device position at the implantation site. For instance, a selected biocompatible agent, when associated with a portion of the medical device surface, can serve to initiate a local fibrotic response to anchor the device in position. One illustrative device can include a first portion where it is desirable to encourage tissue healing (for example, at a device port or anchoring portion of the device), and a second portion where non-thrombogenicity is desirable (for example, at a catheter inner lumen or outer lumen, or a sensor portion of the device). It will be readily appreciated that any number of distinct biocompatible regions can be included on a single device in accordance with the inventive concepts. Moreover, each biocompatible region can include one or more biocompatible agents selected to provide a desired biocompatible function at each such region of the device.

The biocompatible agent can be essentially any reagent that is nonreleasably associated with the solid surfaces of medical articles to improve biocompatibility of the medical article. In preferred aspects, the biocompatible agent is associated with and becomes part of the polymeric matrix at the surface of the medical article. The biocompatible agent is thus immobilized at the surface (as distinguished from being eluted from the surface). The biocompatible agents selected according to the invention thus include agents that can be immobilized within the polymeric matrix and retain activity once so immobilized. The biocompatible agent is preferably a relatively large molecule, such as a polymer that includes amino acid or saccharide monomeric units. Smaller molecules that are non-polymeric, for example, small synthetically prepared or naturally derived molecules can be relatively difficult to nonreleasably associate with the polymeric matrix and therefore are not typically selected as a biocompatible agent according to the invention.

In some aspects the biocompatible agent comprises a polymer, for example a polysaccharide. According to the invention, particularly useful polysaccharides can be selected from mucopolysaccharides such as heparin, hyaluronic acid, chondroitin sulfate, keratan sulfate, and dermatan sulfate.

In some aspects, the biocompatible agent can be conceptualized by function. In some embodiments, the biocompatible agent provides antirestenotic effects, such as anti-proliferative, anti-platelet, and/or antithrombotic effects. In some embodiments, the biocompatible agent can be selected from cell attachment factors, receptors, ligands, growth factors, enzymes, nucleic acids, and the like.

Biocompatible agents having anti-proliferative effects include, for example, angiopeptin, c-myc antisense, and the like.

Representative examples of biocompatible agents having anti-platelet effects include inhibitors of the GPIIb-IIIa platelet receptor complex, which mediates platelet aggregation. GPIIb-IIIa inhibitors can include monoclonal antibody Fab fragment c7E3, also known as abciximab (ReoPrO™), and synthetic peptides or peptidomimetics such as eptifibatide (Integrilin™) or tirofiban (Agrastat™).

Representative examples of biocompatible agents having antithrombotic effects (thrombin inhibitors) include heparin, heparin derivatives, sodium heparin, low molecular weight heparin, high affinity heparin, low affinity heparin, hirudin, lysine, prostaglandins, argatroban, forskolin, vapiprost, prostacyclin and prostacyclin analogs, PPACK-thrombin (D-phenylalanyl-L-propyl-L-arginine chloromethylketone-thrombin), dipyridamole, glycoprotein IIb/IIIa platelet membrane receptor antibody, coprotein IIb/IIIa platelet membrane receptor antibody, recombinant hirudin, bivalirudin thrombin inhibitor (such as commercially available from Biogen, Cambridge, Mass.), chondroitin sulfate, modified dextran, albumin, streptokinase, tissue plasminogen activator (TPA), urokinase, nitric oxide inhibitors, and the like.

Exemplary growth factors include fibroblastic growth factors, epidermal growth factor, platelet-derived growth factors, transforming growth factors, vascular endothelial growth factor, bone morphogenic proteins and other bone growth factors, and neural growth factors.

Exemplary ligands or receptors not discussed otherwise herein include antibodies, antigens, protein A, and protein G.

Exemplary antibiotics include antibiotic peptides.

In some embodiments, the biocompatible agent can be included to assist in maintaining the position of the device once implanted. Illustrative biocompatible agents that can provide these functions include surface adhesion molecules or cell-cell adhesion molecules. Exemplary cell adhesion molecules include attachment proteins such as extracellular matrix proteins including fibronectin, laminin, collagen (for example, (synthetic) recombinant human collagen (Fibro-Gen, South San Francisco, Calif.)), elastin, vitronectin, tenascin, fibrinogen, thrombospondin, osteopontin, von Willebrand Factor (vWF), bone sialoprotein (and active domains thereof), or a hydrophilic polymer such as hyaluronic acid, chitosan or methyl cellulose, and other proteins, carbohydrates, and fatty acids. Exemplary cell-cell adhesion molecules include N-cadherin and P-cadherin and active domains thereof.

In some embodiments, the biocompatible agent can comprise a pro-fibrotic agent that serves to assist in maintaining the position of the device once implanted. According to the invention, the pro-fibrotic agent can be a polymeric or non-polymeric compound. Some of the above described adhesion type agents can be considered "pro-fibrotic" agents. Examples of additional pro-fibrotic polymers include pro-fibrotic cationic polymers, and pro-fibrotic peptides or proteins, for example thrombin, adenine dinucleotide diphosphite (ADP), or convulxin. Other pro-fibrotic agents include platelet factors 1-4, platelet activating factor (acetyl glyceryl ether phosphoryl choline); P-selectin; tissue factor; plasminogen activator initiator-1; thromboxane; procoagulant thrombin-like enzymes including cerastotin and afaâcytin; phospholipase $A_2$; $Ca^{2+}$-dependent lectins (C-type lectin); factors that bind glycoprotein receptors and induce aggregation including aggretin, rhodocytin, aggregoserpentin, triwaglerin, and equinatoxin; glycoprotein Ib agonists including mamushigin and alboaggregin; vWF interacting factors including botrocetin, bitiscetin, cerastotin, and ecarin.

Other factors, including protein factors, that are involved in the clotting cascade include coagulation factors I-XIII (for example, fibrinogen, prothrombin, tissue thromboplastin, calcium, proaccelerin (accelerator globulin), proconvertin (serum prothrombin conversion accelerator), antihemophilic factor, plasma thromboplastin component, Stuart factor (autoprothrombin C), plasma thromboplastin antecedent (PTA), Hageman factor, and fibrin-stabilizing factor (FSF, fibrinase, protransglutaminase)).

According to the invention, the biocompatible agents are modified to include one or more reactive groups, one or more polymerizable groups, or a combination of reactive groups and polymerizable groups. The reactive group(s) and/or polymerizable group(s) allow the biocompatible agents to become associated with, and form a part of, the polymeric matrix at the surface of the medical article.

In some embodiments, the reactive group comprises a latent reactive group. As used herein, a "latent reactive group" refers to a chemical group that responds to an applied external energy source in order to undergo active specie generation, resulting in covalent bonding to an adjacent chemical structure (via an abstractable hydrogen). Preferred groups are sufficiently stable to be stored under conditions in which they retain such properties. See for example, U.S. Pat. No. 5,002, 582 (Guire et al.). Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to a specific applied external ultraviolet or visible light source to undergo active specie generation with resultant covalent bonding to an adjacent chemical structure, for example, as provided by the same or a different molecule. Photoreactive species are those groups of atoms in a molecule that retain their covalent bonds unchanged under conditions of storage but that, upon activation by a specific applied external ultraviolet or visible light source form covalent bonds with other molecules.

Latent reactive (for example, photoreactive) species generate active species such as free radicals and particularly nitrenes, carbenes, and excited states of ketones, upon absorption of electromagnetic energy. Latent reactive species can be chosen to be responsive to various portions of the electromagnetic spectrum, for example, ultraviolet and visible portions of the spectrum.

Photoreactive aryl ketones are preferred, such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm. Exemplary photoreactive groups are described in U.S. Pat. No. 5,002,582 (Guire et al.).

Another illustrative class of photoreactive groups that can be associated with the biocompatible agent includes azides. Suitable azides include arylazides ($C_6R_5N_3$) such as phenyl azide and particularly 4-fluoro-3-nitrophenyl azide, acyl azides (—CO—$N_3$) such as ethyl azidoformate, phenyl azidoformate, sulfonyl azides (—$SO_2$—$N_3$) such as benzensulfonyl azide, and phosphoryl azides ($(RO)_2PON_3$) such as diphenyl phosphoryl azide and diethyl phosphoryl azide.

Diazo compounds constitute another suitable class of photoreactive groups that can be associated with the biocompatible agent and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as 3-trifluoromethyl-3-phenyldiazirine, and ketenes (—CH=C=O) such as ketene and diphenylketene.

Exemplary photoreactive groups and the bonds that can be formed following activation of these groups are shown in Table I.

TABLE I

| Photoreactive Group | Bond Formed |
| --- | --- |
| Aryl azides | Amine |
| Acyl azides | Amide |
| Azidoformates | Carbamate |
| Sulfonyl azides | Sulfonamide |
| Phosphoryl azides | Phosphoramide |
| Diazoalkanes | New C—C bond |
| Diazoketones | New C—C bond and ketone |
| Diazoacetates | New C—C bond and ester |
| Beta-keto-alpha-diazoacetates | New C—C bond and beta-ketoester |
| Aliphatic azo | New C—C bond |
| Diazirines | New C—C bond |
| Ketenes | New C—C bond |
| Photoactivated ketones | New C—C bond and alcohol |

The functional groups of such ketones as described herein are preferred since they are readily capable of undergoing the activation/inactivation/reactivation cycle described herein. Benzophenone is a particularly preferred latent reactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

In some embodiments, the reactive groups can also serve as polymerization initiators. Such use is described herein.

One or more reactive groups can be associated with the biocompatible agent in a number of ways. Preferably, the number of reactive groups associated with each biocompatible agent is sufficient to immobilize the biocompatible agent within the polymeric matrix material, while maintaining the activity of the biocompatible agent (that is, not hampering activity of the biocompatible agent). Typically, when a photoreactive group is associated with a biocompatible agent, the resultant molecule is described as a "photoderivatized" biocompatible agent. For example, when a polysaccharide is associated with a photoreactive group, the resultant molecule is described as photoderivatized polysaccharide.

For instance, photoderivatized polysaccharides, such as heparin ("photoheparin") can be prepared by those skilled in the art, in the manner described in U.S. Pat. No. 5,563,056 (Swan et al., Preparation of Crosslinked Matrices Containing Covalently Immobilized Chemical Species and Unbound Releasable Chemical Species), which describes preparation of photoheparin by reacting heparin with benzoyl-benzoyl-epsilon-aminocaproyl-N-oxysuccinimide in dimethylsulfoxide/carbonate buffer. The solvent was evaporated and the photoheparin was dialyzed against water, lyophilized, and then dissolved in water.

Other photoderivatized biocompatible agents, such as collagen, fibronectin, and laminin can be prepared as described. See, for example, U.S. Pat. No. 5,744,515 (Clapper, Method and Implantable Article for Promoting Endothelialization). As described in this patent, a heterobifunctional crosslinking agent can be used to photoderivatize a protein, such as a biocompatible agent. The crosslinking agent includes a benzophenone photoactivatable group on one end (benzoyl benzoic acid, BBA), a spacer in the middle (epsilon aminocaproic acid, EAC), and an amine reactive thermochemical coupling group on the other end (N-oxysuccinimide, NOS). BBA-EAC is synthesized from 4-benzoylbenzoyl chloride and 6-aminocaproic acid. Then the NOS ester of BBA-EAC is synthesized by esterifying the carboxy group of BBA-EAC by carbodiimide activation with N-hydroxysuccimide to yield BBA-EAC-NOS. Proteins, such as collagen, fibronectin, laminin, and the like can be obtained from commercial sources. The protein is photoderivatized by adding the BBA-EAC-NOS crosslinking agent at a ratio of 10-15 moles of BBA-EAC-NOS per mole of protein. Some illustrative methods for preparing photo-derivatized biocompatible agents are described in the Examples herein.

In the above-described exemplary photoactivatable biocompatible agents, the benzophenone group can be subsequently activated to serve as the reactive group to associate the biocompatible agent with the polymeric matrix. Other reactive groups and methods of associating the reactive group with the biocompatible agent, and the thus-formed reactive biocompatible agent with the polymeric matrix, will be apparent given the teaching of the present disclosure.

In some aspects, the biocompatible agent can include polymerizable groups. In some embodiments, then, the biocompatible agent can comprise a macromer. For example, hyaluronic acid containing polymerizable groups has been described (see U.S. Pat. No. 6,410,044, Chudzik et al.), where hyaluronic acid was dissolved in dry formamide, and TEA and glycidyl acrylate was added to this solution. The reaction mixture was stirred at 37° C. for 82 hours. After exhaustive dialysis against deionized water using MCWO dialyisis tubing, the product was isolated by lyophilization.

Similarly, collagen containing polymerizable groups can be accomplished in various ways. One illustrative method of preparing collagen containing polymerizable groups is described in U.S. Pat. No. 6,410,044, Chudzik et al. Collagen was dissolved in dry formamide, TEA was then added and equilibrated in ice water bath. Acryloyl chloride was added in −/25 gram aliquots. After the final addition, the solution was stirred in ice water bath for 2 hours, removed, and stirred at room temperature for 18 hours. The product was purified by dialysis against deionized water using MWCO dialysis tubing, and isolated by lyophilization.

Another illustrative method of preparing collagen having polymerizable groups is as follows. Bovine Type 1 Collagen is dissolved in 0.012 N hydrochloric acid and stirred for 4 hours at 4° C. Sodium carbonate and sodium bicarbonate are added to this solution and mixed for 60 minutes at 4° C. Acrylic acid N-hydroxysuccinimide is then added, and the reaction mixture is stirred at 4° C. for 24 hours. The final product is purified by dialysis against deionized water using MWCO dialysis tubing, and isolated by lyophilization.

A further illustrative method of preparing collagen macromer is described in the Examples herein.

Similar reactions can be utilized to provide polymerizable groups to other biocompatible agents, such as, but not limited to, hyaluronic acid, heparin, and the like.

In some embodiments, the biocompatible agent can serve as the crosslinkable macromer system of the inventive coatings. According to these aspects of the invention, the biocompatible agent can include polymerizable groups, thus providing the function of the crosslinkable macromer system described elsewhere herein. The biocompatible agent can be provided with any of the polymerizable groups described herein. The resulting polymerizable biocompatible agent can be used as the matrix material, either alone or in combination with other matrix materials described elsewhere herein.

In some aspects, hydrophilic or swellable polymers can be included in the coating containing biocompatible agent. These types of polymers can be useful in biocompatible coatings as they can provide space-filling properties in the coated article. Such materials are also capable of improving article performance by contributing to the overall function of the article, for example, by improving sealant function.

The hydrophilic or swellable polymer can include pendent polymerizable groups and can be used in a method to form a coated layer that can include the biocompatible agents, or can be separate from one or more of the biocompatible agents.

For example, a composition including a hydrophilic or swellable polymer having pendent polymerizable groups and a polymerization initiator can be disposed on a surface of a medical article. A coated layer containing the hydrophilic or swellable polymer can be formed by initiating polymerization of the polymers. Subsequently, a composition including the biocompatible agent can be disposed on the surface. The biocompatible agent can also include polymerizable groups. A coated layer containing the biocompatible agent can be formed on the layer that includes the hydrophilic or swellable polymer by initiating polymerization of the polymers biocompatible agent.

Particularly useful hydrophilic or swellable polymers include poly(vinylpyrrolidone) (PVP), poly(ethylene glycol) (PEG), poly(ethylene oxide), poly(ethyloxazoline), poly(propylene oxide), polyacrylamide (PAA), poly(vinyl alcohol) (PVA), copolymers thereof, and the like. One or more polymerizable groups can be pendent from the swellable polymer. Mixtures of swellable polymers can also be used.

In some aspects, the hydrophilic or swellable polymer can possess thromboresistant properties, such as polyethylene glycol (PEG). In some embodiments, PEG can be utilized as a biocompatible agent that also serves as a macromer of the polymeric matrix. Surfaces covered with PEG have been shown to be biocompatible because PEG's properties that yield nonimmunogenicity, nonantigenicity, and protein rejection. PEG can be modified, for example, by providing photoreactive groups and/or polymerizable groups to the PEG. A coated layer comprising PEG can be formed by disposing a coating composition including acrylated PEG in combination with a polymerization initiator, for example. In cases where PEG is utilized for its passive hydrophilic properties, it will be readily appreciated that inclusion of a separate biocompatible agent (in addition to the PEG) is optional. In some aspects, biocompatible agent can be applied to a portion of a PEG coating layer, thereby providing two biocompatible portions on a device surface, wherein both portions include a first layer of PEG, and only one portion includes a second layer that includes a different biocompatible agent.

While it can be useful to incorporate swellable polymers having pendent polymerizable groups into the biocompatible coatings, swellable polymers without pendent polymerizable groups can also be utilized to form the coating. Therefore, in another aspect of the invention, coating can be formed from a coating composition that includes a swellable polymer, biocompatible agent, and a photoreactive group.

In some embodiments, additional therapeutic agent can be included at one or more portions of the medical article. Such therapeutic agents can be selected to be releasably associated with the polymeric matrix at the surface of the medical article, such that the therapeutic agent is eluted from the medical article during residence in the patient. Typically, such releasably associated agents comprise lower molecular weight agents as compared to the biocompatible agents of the invention. Some illustrative therapeutic agents include smaller molecules having anti-proliferative effects (such as actinomycin D, paclitaxel, taxane, and the like) anti-inflammatory agents (such as dexamethasone, prednisolone, tranilast, and the like), immunosuppressive agents (such as cyclosporine, CD-34 antibody, everolimus, mycophenolic acid, sirolimus, tacrolimus, and the like), smaller molecule antibiotics, and the like. Suitable therapeutic agents have been described, for example, a comprehensive listing of bioactive compounds and therapeutic agents can be found in *The Merck Index*, Thirteenth Edition, Merck & Co. (2001). One of skill in the art, using the guidance of the present description, can readily select therapeutic agents that are suitable to be eluted from the polymeric matrices of the invention.

According to the invention, the surface of a medical article is provided with a polymeric matrix including more than one biocompatible agent, wherein selected biocompatible agents are applied to distinct portions of the medical article to form distinct biocompatible portions selected to accommodate physiologic environments within the body. The polymeric matrix and biocompatible agent can be applied to the medical article surface simultaneously or sequentially, as desired. In some embodiments, a coating solution containing a polymeric matrix material is prepared and applied to the medical article. After this first coating step, a coating solution containing biocompatible agent is applied to the polymeric matrix on the medical article surface. In other embodiments, a coating solution containing both the polymeric matrix material and the biocompatible agent is prepared, and the coating solution is applied to the medical article surface in a simultaneous coating process.

Traditional coating processes for medical articles often involve application of a coating to the surface via a dipping process. This involves preparation of a solution of the material to be applied to the article surface dispersed in a solvent. The implant is then dipped in the solution, and the coated implant is allowed to dry. Following evaporation of the solvent from the implant, the desired coating remains on the dipped surface. Disadvantages of this approach include inability to adequately control the thickness of the resulting coating (for example, the resulting coating can be too thick for some applications), and the inability to adequately control the coating uniformity (for example, the coating can be uneven due to running of the solution when the medical article is removed from the dip solution). Other disadvantages can relate to the inability to adequately coat intricate surface configurations (for example, small holes or lumens of the medical article can be plugged with coating material). Moreover, such coating methods can be labor intensive, which adds to the cost of the final product. In addition, if the solvent is too aggressive, it may not be possible to treat thin materials without causing distortion of damage, for example, if a medical article is fabricated from polyurethane.

Other conventional coating processes suffer from the same and other disadvantages.

In preferred aspects, the inventive methods and articles can overcome one or more of these disadvantages. According to preferred aspects of the invention, the invention can be utilized to provide uniform coatings of any desired thickness. For example, the inventive methods and systems can be utilized to provide conformal coatings having thicknesses in the range of nanometers to microns, such as 100 nm to 10μ or more. The inventive methods can provide improved consistency as compared to conventional techniques for surface preparation, particularly when the surface of the medical article includes intricate surface configurations or surface irregularities that can result from forming of the medical article.

In one illustrative coating technique, coating solutions can be applied using immersion coating procedures. According to this embodiment, coating solutions are prepared by dissolving the components (for example, polymeric matrix material and biocompatible agent) at desired concentrations in solvent (such as deionized water). Parts are immersed in the reagent solution, optionally allowed to dwell in solution (typically for about 5 to 10 minutes, when done), and then illuminated for 60 seconds utilizing a Dymax Blue Wave Spot Cure System (light system commercially available from Dymax Corporation, Torrington, Conn.). The ultraviolet wand of the system can be placed at a distance to provide the parts of the article to be coated with approximately 0.5 to 0.25 mW/cm$^2$ of light in the wavelength range 330-340 μm. The substrate is gently agitated during the 60 seconds of illumination to ensure that the surface is evenly bathed in light. The medical article is then removed from the coating solution. After removal of the medical article from the coating solution, the medical article is rinsed with deionized water, blown with nitrogen gas to remove large drops of solution, then air dried until the solvent is no longer visible (typically at least 2 minutes, up to overnight air drying).

Illumination parameters can be readily selected, based upon such factors as the reagents chosen, the coating method (simultaneous or sequential addition of components of the coating solution), concentrations of individual components of the coating solution, and the like.

In another illustrative coating technique, coating solutions can be applied using spray coating procedures. One such exemplary spray coating procedure utilizes a roller system such as that described in U.S. Patent Publication No. 2004/0062875 (Chappa et al., Advanced Coating Apparatus and Method). The medical article rotator includes a pair of rollers suitable for holding a rollable article, the pair having first and second rollers that are arranged substantially parallel to each other and separated by a gap. The spray nozzle is operationally arranged to produce spray of a coating solution that is directed at the gap and, when the article is not positioned on the pair of rollers, arranged so the majority of the spray is passed through the gap. In use, a coating solution is disposed on the article from the spray nozzle, and the majority of any spray that does not get deposited on the article is passed through the gap. The medical article is then rotated by rotation of the rollers to position a different portion of the article for subsequent application of a coating solution. The coating device can include an ultrasonic spray nozzle, such as that commercially available from Sonotek and described in U.S. Publication No. 2004/0062875 (Chappa et al., Advanced Spray Coating Apparatus and Method).

According to some aspects of the invention, the coating solution can include both the polymeric matrix material and biocompatible agent. The polymeric matrix material and biocompatible agent (containing reactive group) can be obtained in a composition suitable for disposing on the surface of a medical article, or can be combined in a suitable solvent or dispersant to prepare the coating composition.

While the solubility or dispersability of the components can depend upon the types of polymeric matrix material and biocompatible agent chosen, useful solvents and dispersants according to the invention include, but are not limited to, water, alcohols (such as methanol, ethanol, n-propanol, isopropanol, and the like), amides (such as dimethylformamide, N-methylpyrrolidone), ethers (such as tetrahydrofuran, dipropyl ether, dioxolane, and the like). Further, mixed solvent systems can be beneficial in some embodiments, where it may be desirable to provide more than one polymerization initiator in a common solution. For example, a combination of nonionic and charged initiators (such as Compound II and Compound IV in the Examples) can be utilized with a mixed solvent system, such as 75% IPA/25% water. Selection of solvent system can depend upon the biocompatible agent, polymerization initiator, article surface material, and the like factors.

Application of a coating solution that includes both polymeric matrix material and biocompatible agent is accomplished utilizing any of the herein described coating techniques, or any commonly known coating technique. After application of the coating solution to the medical article surface, the medical article is illuminated with light having the appropriate wavelength to thereby couple the coating solution to the medical article surface.

When this simultaneous coating process is utilized, distinct biocompatible portions of the medical article can be created in a number of ways. For example, a first coating solution containing polymeric matrix and a first biocompatible agent (for example, heparin) can be applied to a selected portion of the medical article surface. Thereafter, a second coating solution containing polymeric matrix and a second biocompatible agent (for example, collagen) can be applied to a selected portion of the medical article that is different from the portion provided with heparin. In another exemplary technique, one portion of the medical article surface can be masked during application of the first coating solution. The mask can be positioned and re-positioned during the coating process to allow precision deposition of the coating solutions containing different biocompatible agent at different portions of the medical article surface. Alternatively, or additionally, masking can be done during illumination of the medical article surface, if desired. In this way, only the areas that are illuminated with light will couple the matrix material and biocompatible agent. These masking approaches can be particularly useful when the coating solutions are applied utilizing spray deposition techniques.

Optionally, the coating solution can additionally include initiator (for example, nonpolymeric initiator). The initiator can be included separately or in combination with other components of the coating solution. In some aspects, the initiator can be provided to the substrate prior to application of the polymeric matrix. In these aspects, the surface can be referred to as "primed" with the initiator (that is, initiator can be attached to the surface prior to application of any additional coating components, resulting in a "primed" surface bearing initiator). In other aspects, the initiator can be provided in combination with other components of the coating solution. Some embodiments of these aspects are illustrated in the Examples.

In alternative embodiments, a sequential coating process can be utilized for application of the polymeric matrix and biocompatible agent to the medical article. According to these embodiments, the polymeric matrix is first applied to the medical article surface, and the biocompatible agent is subsequently provided to the polymeric matrix material.

According to these embodiments, the polymeric matrix material can be provided to the entire medical article surface, or less than the entire medical article surface, as desired. When provided to less than the entire medical article surface, the polymeric matrix material can be applied to selected portions of the article by controlled application techniques, for example, as described above.

Application of the biocompatible agent to the polymeric matrix (and thus the medical article) can be accomplished utilizing any known application technique. For example, in some embodiments, the biocompatible agent is applied to the polymeric matrix by dip coating the medical article in the biocompatible agent, and activating the photoreactive groups while the medical article is dipped into the biocompatible agent. In other illustrative embodiments, the biocompatible agent can be applied in admixture with a solvent. The biocompatible agent can be applied by spray coating the admixture of the biocompatible agent in a solvent. The solvent can be any suitable solvent, as described herein, for example, THF. Any of the coating techniques described herein, as well as other known techniques, can be utilized to apply the polymeric matrix and/or biocompatible agent.

According to the invention, the reactive group associated with the biocompatible agent is activated to associate the biocompatible agent with the medical article. An activated group can cause the bonding of components of the composition to each other, or to the medical article surface with which it is in contact, or both. For example, a reactive group associated with the biocompatible agent can react with the polymeric matrix material and/or the medical article surface with which it is in contact to form a covalent bond. In some embodiments, the reactive group is a photoreactive group, and the step of activating involves providing irradiation in a manner sufficient to activate the photoreactive groups. In some cases, activation energy can be applied more than one time during the coating process.

Illumination of the coating solution can be performed in a number of manners. In some aspects, the coating solution can be illuminated without an intermediate drying step. This can, in preferred aspects, reduce the number of coating steps required, thus increasing the efficiency of coating methods and systems. In other aspects, coating solutions can be applied and dried before illuminating the coating solutions on the surface.

It will be understood that a particular portion of a medical article surface can include more than one biocompatible agent, if desired. Inclusion of more than one biocompatible agent at a particular portion of the medical article can be desired, for example, when the biocompatible agents provide a synergistic biocompatible function at the application site. For example, more than one pro-fibrotic agent can be included at a particular portion of the medical article, such that the pro-fibrotic agents provide an enhanced fibrotic function at that portion.

In some embodiments, grafting techniques can be utilized to provide the biocompatible agent and polymeric matrix at the surface of the medical article. In some aspects, such grafting techniques can utilize a nonpolymeric initiator as described herein. For example, a coating agent such as 4,5-bis(4-benzoylphenylmethyleneoxy)benzene-1,3-disulfonic acid disodium salt (DBDS) can be provided at a desired concentration in water and applied to a medical article surface (for example, by spraying). The article surface is illuminated with light for a selected time and at a selected intensity to associate the coating agent with the article surface. The article surface can then be placed in a solution containing polymeric matrix material (such as PEG) and illuminated for a desired time and at a desired intensity to associate the polymeric material with the article surface. A more specific method is described in the Examples.

In some aspects, the inventive methods and systems can include application of a photoreactive polymer at one or more portions of the article surface. A photoreactive polymer can be utilized, for example, to optionally enhance application of other coating components described herein to the medical article surface. Suitable photoreactive polymers include polymeric materials that include photoreactive groups, including any of the photoreactive groups described elsewhere herein. One illustrative photoreactive polymer is photo-polyvinylpyrrolidone ("photo-PVP"). An exemplary method of making and applying a photo-PVP layer to a medical article surface is described in the examples. In one embodiment, for example, a photoderivatized PVP can be prepared by the copolymerization of 1-vinyl-2-pyrollidone and N-(3-aminopropyl)methacrylamide. The copolymers are derivatized with an acyl chloride (such as, for example, 4-benzoylbenzoyl chloride) under Schotten-Baumann conditions and the unreacted amines of the polymer can be acetylated using acetic anhydride to give an acetylated photo-PVP. That is, the acyl chloride reacts with some of the amino group of the N-(3-aminopropyl) moiety of the copolymer, resulting in the attachment of the aryl ketone to the polymer. The liberated hydrochloric acid is neutralized with an aqueous base solution. The resulting acetylated photo-PVP is commercially available, for example, under the product name "PV05" from SurModics, Inc., Eden Prairie, Minn., or can be synthesized. One of skill in the art, upon review of the present disclosure, will readily appreciate that other photoreactive polymers can be used as well.

Although not required, typical application of the coating components to a surface will involve providing a photoreactive polymer to a surface prior to application of polymeric matrix material and/or other coating components. In these aspects, the surface can be referred to as "primed" with the photoreactive polymer (that is, photoreactive polymer can be attached to the surface prior to application of other coating components, resulting in a "primed" surface bearing photoreactive polymer). Some photoreactive polymers are commercially available from SurModics, Inc., Eden Prairie.

A "coating" as described herein can include one or more "coated layers," each coated layer including one or more coating components. In some cases, the coating includes a polymeric matrix layer containing biocompatible agent in addition to one or more layers. If more than one coated layer is applied to the surface of a medical article, it is typically applied successively. For example, a coating is typically formed by dipping, spraying, or brushing the coating solution on a medical article to form a layer, and then drying the coated layer. The process can be repeated to provide a coating having multiple coated layers, wherein at least one layer includes a polymeric material and a biocompatible agent. For example, the polymeric matrix material and biocompatible agent can be present in a coating along with a base coat and/or top coat. The other layers can be the same or different than the coating containing polymeric matrix and biocompatible agent. The suitability of the coating composition for use with a particular medical article, and in turn, the suitability of the application technique, can be evaluated by those skilled in the art, given the present description.

In preferred aspects, the invention provides flexibility in terms of coating processes and systems, since any one or more components of a desired coating can be combined and applied to selected medical article portions. For example, coating compositions can be prepared that include all desired coating components (such as polymeric matrix material, biocompatible agent, and optionally, initiator), and the coating compositions can be applied to a medical article surface in a controlled manner. In some aspects, coating compositions can be prepared and sequentially applied, such that priming layers are provided at selected surfaces of a medical article, followed by layers of desired components (such as polymeric matrix material, biocompatible agent, and the like). Some illustrative combinations of coating techniques are given in the Examples.

The inventive coatings and methods can be utilized in combination with any desired medical article. Moreover, the coating compositions described herein can be applied and coupled with a wide variety of materials at the article surface. In some embodiments, the medical article can be fabricated from any suitable material used to manufacture medical articles, such as, for example, stainless steel (for example, 316L); platinum; titanium; and gold; and such alloys as cobalt chromium alloys, nitinol, or the like. In further embodiments, suitable ceramics can be used to fabricate the medical article, such as, for example, silicon nitride, silicon carbide, zirconia, alumina, glass, silica, sapphire, and the like. In still further embodiments, the medical article can be fabricated of a suitable composite material, such as those composite materials commonly used to fabricate medial articles. Such composite materials can, in some embodiments, provide such advantages as increased strength of the material, as well as increased flexibility. Examples of suitable composite materials include polymers or ceramics (such as high density polyethylene (HDPE), ultra high molecular weight polyethylene (UHMWPE), polymethylmethacrylate bone cement (PMMA), dental polymer matrix (such as crosslinked methacrylate polymers), and glass-ceramics) reinforced with fibers or particulate material (such as carbon fibers, bone particles, silica particles, hydroxyapatite particles, metal fibers or particles, or zirconia, alumina, or silicon carbide particles). Nano-composite materials are also contemplated.

In one embodiment, the medical article is fabricated of a nonbiodegradable polymer. Such nonbiodegradable polymers are well known and can include, for example, oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; and vinyls such as ethylene, propylene, styrene, vinyl chloride, vinyl acetate, and vinylidene difluoride. Examples of condensation polymers include, but are not limited to, nylons such as polycaprolactam, polylauryl lactam, polyhexamethylene adipamide, and polyhexamethylene dodecanediamide, as well as polyurethanes, polycarbonates, polyamides (including polyether-based polyamides such as PEBAX), polysulfones, poly (ethylene terephthalate), polylactic acid, polyglycolic acid, polydimethylsiloxanes, and polyetherketone. Other suitable nonbiodegradable polymers include silicone elastomers; silicone rubber; polyolefins such as polypropylene and polyethylene; homopolymers and copolymers of vinyl acetate such as ethylene vinyl acetate 2-pyrrolidone copolymer; polyacrylonitrile butadiene; fluoropolymers such as polytetrafluoroethylene (including ePTFE) and polyvinyl fluoride; homopolymers and copolymers of styrene acrylonitrile; homopolymers and copolymers of acrylonitrile butadiene styrene; polymethylpentene; polyimides; natural rubber; polyisobutylene; polymethylstyrene; latex; and other similar nonbiodegradable polymers.

As discussed elsewhere herein, the polymer of the medical article can be a hydrophobic polymer. In these aspects, the inventive methods and systems can provide significant advantages.

As described herein, the inventive coating solutions can be applied as aqueous coating solutions. In some aspects, then, the inventive methods can utilize relatively mild coating conditions, as compared to coating solutions that utilize organic solvents. It is known that organic solvents can adversely impact any proteins present in a system, for example by denaturing the proteins. Thus, utilization of aqueous coating systems can be beneficial in retaining biocompatible agent stability in the coating compositions, as discussed. These same concepts apply to the material used to fabricate the surface of the medical articles as well. In some embodiments, additives, such as proteins (e.g., enzymes) could be included in a substrate material, thereby providing a protein at the medical article surface. One illustrative embodiment of such an arrangement is a sensor, wherein the material used to fabricate the sensor includes a protein. In these aspects, the inventive methods and systems would not adversely impact (for example, by denaturing) any proteins included in the substrate material of the medical article itself.

Also, with regard to sensor components, these components are often composed of fragile materials. For example, sensors can be fabricated from polymers that are inherently less durable than polymers typically used to fabricate structural components (such as a catheter component) of a device. Further, the sensor material can be porous, to allow bodily materials to contact the sensor device adequately. One of skill in the art will readily appreciate that the relatively mild coating conditions described herein can be particularly beneficial when it is desirable to provide a biocompatible coating to a medical article that includes a sensor component.

In some embodiments, the medical article can be fabricated of a material having shape memory and/or superelastic characteristics that allow the device to be deformed into a configuration that is more easily inserted into the body. In one such embodiment, for example, the medical article can be deformed into a substantially linear configuration, for insertion into the body. According to this particular embodiment, the implantable device can return to its original shape after it is inserted into the body. In this embodiment, the medical article has a "memory shape" that it will assume under certain conditions. For example, the implantable device can have a coiled memory shape. When the interventionalist desires to implant the device into the body, the interventionalist can deform the device into a substantially linear shape for insertion of the device through an incision the size of the cross section of the linear shaped device. Upon implantation of the device into the body, the device can then resume its coiled or other memory shape. Preferably, the overall dimensions of the implantable device (the maximum length and width) according to these shape memory embodiments do not significantly change by virtue of utilization of the shape memory material and deformation of the body of the implantable device for implantation and/or explantation of the device in the body.

Shape memory alloys generally have at least two phases, namely, a martensite phase, which has a relatively low tensile strength and which is stable at relatively low temperatures, and an austenite phase, which has a relatively high tensile strength and which is stable at temperatures higher than the martensite phase. The shape memory characteristics are imparted to the material by heating the material to a temperature above the temperature at which the austenite phase is stable. While the material is heated to this temperature, the device is held in the "memory shape," which is the shape that is desired to be "remembered." Materials having shape memory and/or superelastic characteristics are well known and can include, for example, shape memory alloys (SMA) such as nitinol (a nickel-titanium alloy), and shape memory polymers (SMP) such as AB-polymer networks based upon oligo(e-caprolactone) dimethylacrylates and n-butyl acrylate. Such materials and methods of imparting shape memory characteristics are known and will not be described further herein.

For purposes of illustration of the invention, a transmyocardial catheter will be described. Typically, a transmyocardial catheter includes four implantable components, namely, a pressure transmitting catheter, remote sensor assembly, leads connecting the remote sensor assembly to a telemetry unit, and a telemetry unit that houses the power source and transmits, via telemetry, pressure data to the remote transceiver. The pressure transmitting catheter is designed to be inserted directly through the left ventricular wall during open-chest procedures. The pressure transmitting catheter is filled with fluid and sealed at the distal end with a biocompatible silicone gel. The gel transmits the pressure from the left ventricle to the fluid in the catheter, which then transmits it to the remote sensor assembly. The remote sensor assembly is typically provided in a titanium housing, with approximate dimensions of 14 mm (height), 25 mm (diameter), and contains the pressure sensor and an electronics module for signal processing. The remote sensor assembly samples left ventricular pressure at 500 Hz. The remote sensor assembly is attached to the heart (for example, using sutures) via the epicardium. Typically, the telemetry unit is placed in the upper abdominal wall or peritoneal cavity.

In use, left ventricular pressure information is transmitted from the remote sensor assembly to the lead, and then to the telemetry unit. The telemetry unit then transmits the information via telemetry to an external remote transceiver. The implanted components are completely contained within the patient, with no exit wounds, thereby minimizing infection risk during residence of the device.

The various components of the catheter can be fabricated from, and/or coated with, different materials. For example, the pressure transmitting catheter can consist of a polyurethane-polycarbonate inner extrusion with an ePTFE outer extrusion covering. The lumen of the polyurethane extrusion can contain a pressure transmission fluid that is capped off at the distal tip with a crosslinked silicone gel. Thus, the pressure transmitting catheter portion of the medical article alone can include more than one surface material (ePTFE and silicone). The telemetry unit is typically contained within a titanium housing.

If desired, the transmyocardial catheter can be washed prior to application of a coating. Such washing can be performed, if desired, to remove contaminants and would involve standard solvents commonly used to wash such devices.

In one illustrative embodiment, a PEG/collagen coating can be associated with the ePTFE material, while PEG/heparin coating can be associated with the polyurethane and silicone gel tip. The coatings are cured, the device is packaged for sterilization, and the device is sterilized using suitable methods (such as EtO sterilization).

Accordingly, a PEG/collagen coating is provided in association with a portion of the device constructed to be inserted directly through the left ventricular wall and reside therein during use within a patient. The PEG collagen coating can improve cell adhesion during use of the device, thus assisting in anchoring the overall device in place within heart muscle during monitoring of a patient. For the same device, a PEG/heparin coating is provided in association with a portion of the device constructed to reside within the left ventricle during use of the device within a patient. The polyurethane and silicone gel tip is provided with a PEG/heparin coating to enhance performance of the overall device by providing any of the activities associated with heparin, including providing local catalytic activity to inhibit several enzymes critical to the formation of fibrin (which holds thrombi together), reducing the adsorption of blood proteins, many of which lead to undesirable reactions on the medical article surface, and/or reducing the adhesion and activation of platelets, which are a primary component of thrombus.

Biocompatible function can be assessed in a variety of manners. The following assays provide exemplary techniques for assessing function of portions of a medical article surface.
Heparin Activity Assay The antithrombotic activity of heparin is due to its inhibition of thrombin, which is a protease that is known to participate in the clotting cascade. Heparin inhibits thrombin activity by first binding to antithrombin III (ATIII). The heparin/ATIII complex then binds to and inactivates thrombin, after which the heparin is released and can bind to another ATIII. The assay for inhibition of thrombin by immobilized heparin can be conducted by measuring the cleavage of a chromogenic peptide substrate by thrombin.

Prior to performing the Heparin Activity Assay, parts are typically washed overnight (12-18 hours) to remove any unbound material from the substrates. Parts are washed in diH$_2$O or PBS at a temperature in the range of 20-30° C. on an orbital shaker (set for gentle agitation).

A typical heparin assay can be performed as follows. Each assay is conducted in an appropriate volume of PBS that contains BSA, human thrombin, ATIII, and chromogenic thrombin substrate. For example, an illustrative assay solution is: 0.85 mg BSA (Sigma Chemical Co.), 10 mU human thrombin (Sigma Chemical Co.), 100 mU/ml ATIII (Baxter Biotech, Chicago, Ill.), and 0.17 µmole of the chromogenic thrombin substrate S-2238 (Kabi Pharmacia, Franklin, Ohio). To this assay solution is added either uncoated or heparin coated devices (to evaluate heparin activity on the membranes) or standard concentrations of heparin (to generate standard curves of heparin content versus absorbance). The color generated, measured as absorbance at 405 nm, by thrombin mediated cleavage of the S-2238 is read using a spectrophotometer after 2 hours of incubation at 37° C. The absorbance is directly related to the activity of the thrombin and, thus, inversely related to the amount of activation of ATIII induced by the heparin in solution or immobilized on the surface of the substrate. Activity of surface bound heparin can be calculated by comparing the absorbance values generated with the membranes to the absorbance values generated with known amounts of added heparin.
Thrombosis Assay Thrombogenic behavior can be identified by a number of events. One way of identifying thrombogenic behavior is by observing reduced blood clotting. Another way of identifying thrombogenic behavior is by measuring the differential between the systolic and diastolic pressure (hereinafter referred to as the pulse pressure difference). For example, the pulse pressure difference can drop by at least about 10 mm Hg when thrombosis begins to clog the fluid flow path of a catheter.

EXAMPLES

The following reagents are used in the Examples:
Luviskol™ K90 (polyvinylpyrrolidone, MW 1,200,000-2,000,000, BASF, Germany)
Luviskol™ K30 (polyvinylpyrrolidone, MW 45,000-55,000, BASF, Germany)
The following compounds are described in the Examples.

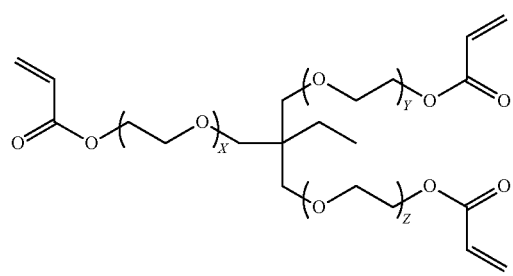
Compound I: PEG-triacrylate macromer
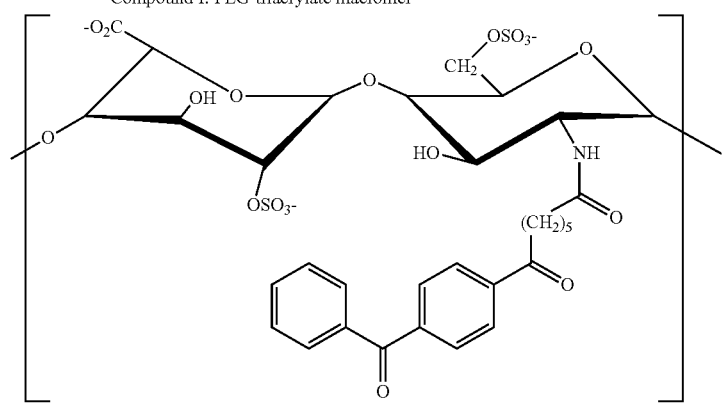
Compound II: (BBA-EAC-Heparin; photo-heparin)
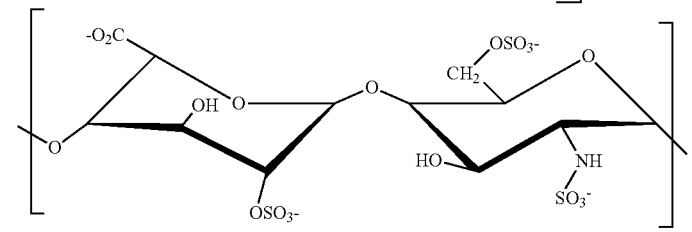
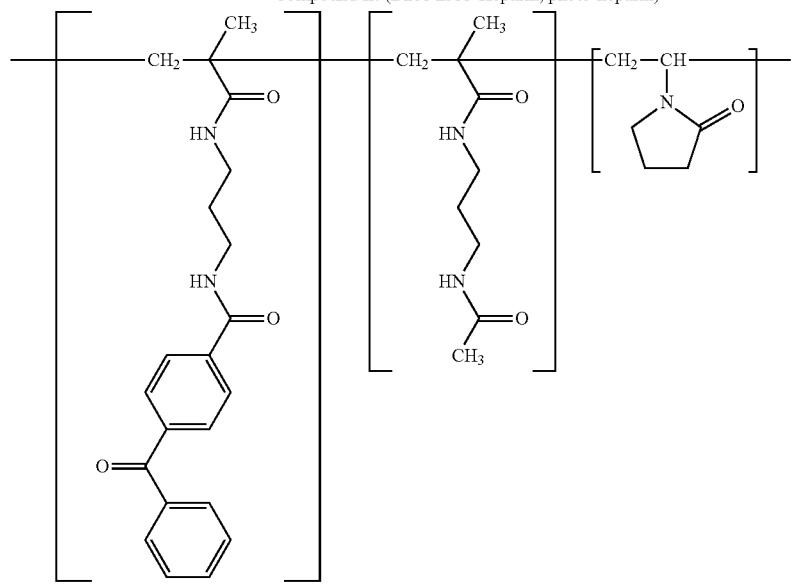
Compound V(Acetylated PVP-APMA-BBA)(Acetylated Photo-PVP)

Example 1

Preparation of a Trimethylolpropane Ethoxylate (20/3 EO/OH) Triacrylate Macromer (Compound I)

A PEG-based macromer was synthesized as follows (synthesis scheme represented at the end of this Example).

Trimethylolpropane ethoxylate (PEG-triol; 100.0 g, 98.6 mmoles; Average $M_w$ approximately 1,104; Cat. No. 41,617-7; Aldrich Chemical Company, Inc., Milwaukee, Wis.) was dissolved in 200 mls of toluene with stirring and refluxed for one hour. The PEG-triol solution was allowed to cool to approximately 80° C. At this time, 50 mg (0.403 mmoles) of 4-methoxyphenol (MEHQ; J. T. Baker, Phillipsburg, N.J.), 42.7 g (0.592 moles) of acrylic acid (J. T. Baker, Phillipsburg, N.J.), and 10 mls (0.188 moles) of sulfuric acid (Aldrich Chemical Company, Inc., Milwaukee, Wis.) were added with stirring to the reaction solution. The reaction solution was heated to reflux. The reaction was allowed to progress until about 6.0 mls of water was produced and collected via a Dean & Stark receiver (approximately one hour). The reaction mixture was allowed to cool to 50° C. and poured into a solution of sodium bicarbonate (270 g in 2.5 liters of deionized water) with stirring. The organic layer was separated, washed with deionized water and dried over sodium sulfate. The PEG-triacrylate was isolated using a wiped film still (Pope Scientific, Inc., Saukville, Wis.).

A PEG-triacrylate macromer product is represented by Compound I.

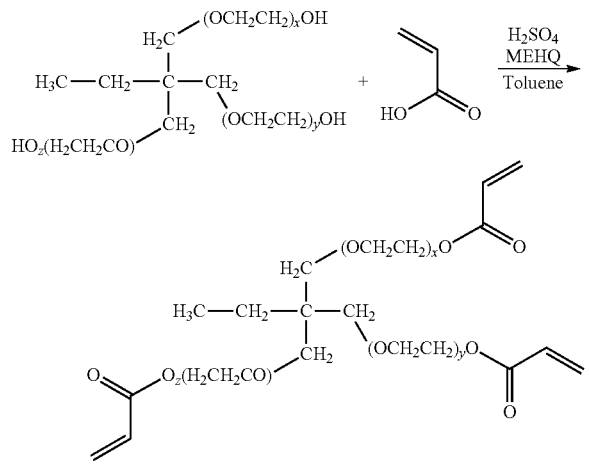

Example 2

Preparation of Photoheparin (Compound II)

A photoreactive derivative of heparin (photoheparin) was prepared by reacting heparin with benzoyl-benzoyl-epsilon-aminocaproyl-N-oxysuccinimide in dimethylsulfoxide/carbonate suffer, pH 9.0. The solvent was evaporated and the photoheparin was dialyzed against water, and lyophilized, and then dissolved in water at 3 mg/ml. The product is referred to as BBA-EAC-heparin (referring to the benzophenone photoreactive group benzoyl benzoic acid, BBA; and the spacer, epsilon aminocaproic acid, EAC).

Example 3

Preparation of Photocollagen

A photoreactive derivative of type IV collagen (photocollagen) was prepared as follows. Human placental type IV collagen was obtained from Sigma Chemical Co., St. Louis, Mo. A heterobifunctional crosslinking agent (BBA-EAC-NOS) was synthesized and used to photoderivatize the collagen.

The BBA-EAC-NOS includes a benzophenone photoreactive group (BBA), a spacer (EAC) and an amine reactive thermochemical coupling group (N-oxysuccinimide, NOS). BBA-EAC was synthesized from 4-benzoylbenzoyl chloride and 6-aminocaproic acid. Then the NOS ester of BBA-EAC was synthesized by esterifying the carboxy group of BBA-EAC by carbodiimide activation with N-hydroxysuccinimide to yield BBA-EAC-NOS.

Type IV collagen was photoderivatized by covalently coupling primary amines on the protein via the NOS ester of BBA-EAC-NOS. The BBA-EAC-NOS was added at a ratio of 10-15 moles of BBA-EAC-NOS per mole of collagen.

Example 4

Preparation of Nonpolymeric Initiator 4,5-bis(4-benzoylphenylmethyleneoxy)benzene-1,3-disulfonic acid disodium salt [DBDS] (Compound IV)

4,5-bis(4-benzoylphenylmethyleneoxy)benzene-1,3-disulfonic acid disodium salt (DBDS) was prepared as follows. An amount (9.0 g, 0.027 moles) of 4,5-dihydroxy 1,3-benzene disulfonic acid disodium salt monohydrate was added to a 250 ml, 3 necked round bottom flask fitted with an overhead stirrer, gas inlet port, and reflux condenser. An amount (15 g, 0.054 moles) of 4-bromomethylbenzophenone (BMBP), 54 ml tetrahydrofuran (THF), and 42 ml deionized water were then added. The flask was heated with stirring under an argon atmosphere to reflux. The argon atmosphere was maintained during the entire time of refluxing.

After reflux was reached, 9.0 ml (6N, 0.054 moles) of a sodium hydroxide solution was added through the reflux condenser. The reaction was stirred under reflux for 3 hours. After this time, a second portion of BMBP, 3.76 g (0.014 moles), and 3.6 ml (6N, 0.022 moles) of sodium hydroxide were added. The reaction was continued under reflux for more than 12 hours, after the second BMBP addition.

The reaction mixture was evaporated at 40° C. under vacuum on a rotary evaporator to give 46 g of a yellow paste. The paste was extracted by suspending three times in 50 ml of chloroform at 40° C. for 30 minutes. A centrifuge was used to aid in the decanting of the chloroform from the solid. The solid was collected on a Buchner funnel, after the last extraction, and air dried for 30 minutes. The solid was then dried by using a rotary evaporator with a bath temperature of 50° C. at a pressure of about 1 mm for 30 minutes.

The dried solid, 26.8 g, was recrystallized from 67 ml of water and 67 ml of methanol. The dried purified product amounted to 10.4 g (theoretical yield was 19.0 g) with absorbance of 1.62 at 265 nm for a concentration of 0.036 mg/ml.

Example 5

Preparation of Nonpolymeric Initiator Tetrakis(4-benzoylbenzyl ether) of Pentaerythritol ["tetra-BBE-PET"] (Compound III)

The following were refluxed for 34 hours in an argon atmosphere:

Pentaerythritol [Aldrich] (2.0 g; 14.71 mmole, dried at 60° C. at <1 mm Hg for one hour);
4-bromomethylbenzophenone (20.0 g; 72.7 mmole; prepared by free radical bromination of 4-methylbenzophenone [Aldrich]);
80% (w/w) sodium hydride in mineral oil [Aldrich] (NaH, 1.23 g; 41.0 mmole); and
Tetrahydrofuran (THF, 120 ml).

An additional amount of 80% NaH (2.95 g; 98.3 mmole) was then added to the reaction mixture, and the mixture refluxed for an additional 7 hours under argon. The reaction was quenched by the addition of 8 ml of glacial acetic acid (HOAc). The quenched reaction was centrifuged to aid in the removal of THF insolubles.

The liquid was decanted, and the insolubles were washed with three 50 ml portions of chloroform ($CHCl_3$). The decanted liquid (mainly THF) and the $CHCl_3$ washes were combined and evaporated to give 18.7 g of a crude yellow semi-solid residue. A portion of the crude product (2 g) was purified by flash chromatography, using a 40 mm (1.58 inch) diameter by 200 mm (8 inch) long silica gel column eluted with $CHCl_3$ and diethyl ether ($Et_2O$) according to the following Table 2 (unless otherwise indicated, all ratios in the table are v/v):

TABLE 2

| Solvent (v/v) | Solvent volume (ml) | Fraction Numbers |
| --- | --- | --- |
| $CHCl_3$ - 100 | 500 | 01-22 |
| $CHCl_3/Et_2O$ - 98/2 | 500 | 23-46 |
| $CHCl_3/Et_2O$ - 95/5 | 1000 | 47-93 |
| $CHCl_3/Et_2O$ - 90/10 | 500 | 94-118 |

A light yellow oily product (0.843 g; 59% theoretical yield) was obtained by combining and evaporating fractions 81-105 (In theory, a yield of 1.43 g tetra-BBE-PET would be expected from 2.0 g of the crude product placed on the column). The purified light yellow product was confirmed by analysis using a Beckman Acculab 2 infrared spectrometer and a Varian FT-80 NMR spectrometer. The absence of a peak at 3500 cm-1 indicated the absence of hydroxyl functionality. Nuclear magnetic resonance analysis ($^1H$ NMR ($CDCl_3$)) was consistent with the desired product; aliphatic methylenes $\delta$ 3.6 (s, 8H), benzylic methylenes $\delta$ 4.5 (s, 8H), and aromatics $\delta$ 7.15-7.65 (m, 36H) versus tetramethylsilane internal standard.

The product is referred to as tetrakis(4-bezoylbenzyl ether) of pentaerythritol (tetra-BBE-PET).

Example 6

Preparation of Nonpolymeric Initiator Tetrakis(4-bezoylbenzoate ester) of Pentaerythritol [tetra-BBA-PET]

Pentaerythritol [Aldrich] (136 mg; 1 mmole), 4-benzoylbenzoyl chloride (1.0 g; 4.09 mmole; prepared by the reaction of thionyl chloride and 4-benzoylbenzoic acid [Aldrich]), triethylamine [Aldrich] (696 ml; 5 mmole), and chloroform (10 ml) were stirred overnight at room temperature. The reaction mixture was placed in ice cold hydrochloric acid (0.5 M; 11 ml) and thoroughly mixed for 1 minute. The chloroform layer was separated, dried over sodium sulfate, and evaporated, yielding an orange residue (1.13 g). The residue was purified by flash chromatography using a 40 mm (1.57 inch) diameter by 180 mm (7 inch) long silica gel column, which was eluted with chloroform/acetonitrile, 96:4 (v/v). Seventy-two 13 ml fractions were collected. Fractions 37 to 61 were combined and evaporated to give a white solid (322 mg; 33% of theory). Analysis on a Varian FT-80 NMR spectrometer was consistent with the desired product: $^1H$ NMR ($CDCl_3$); aliphatic methylenes $\delta$ 4.7 (s, 8H) and aromatics $\delta$ 7.15-8.10 (m, 36 H) versus tetramethylsilane internal standard.

The product, a tetrakis(4-bezoylbenzoate ester) of pentaerythritol (tetra-BBA-PET) includes ester groups as linkages.

Example 7

Surface Modification of Silicone Substrates by Application of Nonpolymeric Initiator and Subsequent Grafting of Polymeric Matrix A polymeric matrix was provided on the surface of a silicone substrate by applying a nonpolymeric initiator to the surface, followed by grafting of a polymeric matrix to the surface. Compound IV (as prepared in Example 4) was applied using a spray method, followed by grafting with methoxy PEG 1000 MMA (polyethylene glycol monomethacrylate) on a silicone substrate as follows.

A silicone substrate was mounted on a rotator (set at 100 revolutions per minute, rpm). The rotator was then placed under a spray and UV light source. The spray was angled at approximately 45° from horizontal and was 4.5 cm from the rounded edge of the mounting.

A solution of Compound IV at a concentration of 0.5 mg/ml in water was sprayed onto the substrate at a constant rate of 4-5 ml per minute. A nitrogen environment was maintained throughout the application of Compound IV by introducing a nitrogen stream into the system. Simultaneously, the substrate was illuminated with an Oriel Series Q Arc Lamp (Oriel Instruments, Stratford, Conn.) that contained an Osram HBO 100 $W/cm^2$, mercury short arc doped bulb (Germany). The substrate was illuminated for 30 seconds at an intensity of 20 $mW/cm^2$ in the wavelength range of 330-340 nm. The UV bulb was placed at a 45° angle from horizontal.

After Compound IV was sprayed onto the substrate, three coated substrates were placed in 8 ml of a 25% methoxy PEG 1000 (v/v in water) solution contained in a 20 ml Fortuna syringe. The methoxy PEG 1000 solution and substrates were then deoxygenated using nitrogen gas bubbling up from the bottom of the syringe for 15 minutes. During the last 5 minutes, an EFOS UV light (Engineered Fiber Optics System, Model No. 100 SS Plus, EFOS U.S.A. Inc., Williamsville, N.Y.) was placed at the top of the syringe. The solution was illuminated with the EFOS while nitrogen gas was still bubbling up through the PEG solution. The solution was illuminated for 5 minutes at an intensity of 4-6 $mW/cm^2$, with a 320-500 nm filter at the level of the PEG solution.

The product was a silicone substrate having PEG polymeric chains attached to a surface.

It was observed that reducing the acrylate level can increase the rate of grafting versus the rate of polymeric matrix formation in-solution.

Example 8

Surface Modification of ePTFE Substrates by Sequential Application of Initiator, Polymeric Matrix Material, and Photoderivatized Biocompatible Agent An ePTFE substrate is first primed with nonpolymeric initiator as follows. A coating solution of Compound III (prepared as described in Example 5) is prepared having a concentration of 0.5% v/v in IPA. The substrate is immersed in the coating solution of Compound III and illuminated in-solution 3 minutes midway between two opposed ELC-4000 lamps containing 400 watt metal halide/mercury vapor bulbs separated by a distance of 91 cm (36 inches). After a rinse with IPA to remove unbound Compound III, the substrate is allowed to dry. The resulting substrate contains a priming coating of Compound III.

After drying, the primed and dried substrate is dipped into a solution of Compound I (prepared as described in Example 1) having a concentration of approximately 10-20% v/v in IPA. The substrate is subsequently withdrawn from the Compound I solution at a rate of 0.2 to 1.0 cm/s. The coated part is again illuminated, wet or dry, for 3 to 5 minutes (as described above).

The substrate is then dipped and subsequently withdrawn at a rate of 0.2 to 1.0 cm/s from a solution containing Compound II (prepared as described in Example 2) in IPA (approximately 5 to 20% v/v). The substrate is again illuminated wet or dry, for 3 to 5 minutes.

Example 9

Surface Modification of ePTFE Substrates by Sequential Application of Initiator, Polymeric Matrix Material, and Photoderivatized Biocompatible Agent An ePTFE substrate is first primed with nonpolymeric initiator as follows. A coating solution of Compound III (prepared as described in Example 5) at a concentration of 0.5% v/v in IPA is prepared. The ePTFE substrate is then immersed in the coating solution of Compound III and illuminated in-solution for 3 minutes. Illumination is performed for 3 minutes midway between two opposed ELC-4000 lamps containing 400 watt metal halide/mercury vapor bulbs separated by a distance of 91 cm (36 inches). After a rinse with IPA to remove unbound Compound III, the substrate is allowed to dry. The resulting substrate contains a priming coating of Compound III.

After drying, the primed and dried substrate is dipped into a solution containing Compound I and Compound III in water (concentration Compound I is approximately 10-20% v/v, and Compound III is approximately 0.5-2% v/v). The substrate is withdrawn at a rate of 0.2 to 1.0 cm/s. The coated part is again illuminated, wet or dry, for 3 to 5 minutes (as described above).

The substrate is then dipped and subsequently withdrawn at a rate of 0.2 to 1.0 cm/s from a solution containing Compound II (prepared as described in Example 2) or photocollagen (prepared as described in Example 3) in IPA, at biocompatible agent concentrations of approximately 5-20% v/v. The substrate is again illuminated, wet or dry, for 3 to 5 minutes.

Example 10

Surface Modification of PEBAX Substrates by Application of Polymeric Matrix Material/Initiator to Substrate A solution containing both polymeric matrix and initiator was prepared and applied simultaneously to PEBAX substrates as follows.

Aqueous coating solutions containing Compound I and Compound IV were prepared including 10% v/v Compound I and 10 mg/ml Compound IV (Compound I prepared as described in Example 1, and Compound IV prepared as described in Example 4). A PEBAX (Modified Polymer Components, Inc., Sunnyvale, Calif.; polyether-based polyamide) substrate was dipped in the solution of Compound I/Compound IV at the rates identified in the following Table 3. The substrate was then illuminated, wet or dry, for the time identified in the following Table 3 midway between two opposed ELC-4000 lamps containing 400 watt metal halide/mercury vapor bulbs separated by a distance of 91 cm (36 inches).

TABLE 3

| Sample No. | Coating rates (cm/s) | Illumination time (minutes) | Coating applications |
|---|---|---|---|
| 47 | 0.2 | 6 | 1 |
| 48 | 0.5 | 7 | 1 |
| 49 | 0.75 | 8 | 1 |
| 50 | 0.5 | 7 | 2 |
| 51 | 0.75 | 7 | 3 |
| 52 | 0.5 | 7 | 3 |

It was observed that dip coating speeds in the range of 0.2 cm/s to 0.75 cm/s produced suitable coatings on the substrates. The higher dip coating speeds (0.5 to 0.75 cm/s) produced thicker coatings and 0.2 cm/s. Moreover, for substrates that received multiple coatings (2-3 coating applications as in Samples 50-52), the resulting coatings were found to provide improved coatings over substrates that received a single coating.

Example 11

Surface Modification of ePTFE Substrates by Simultaneous Application of Polymeric Matrix Material and Initiator Coating solutions containing both polymeric matrix material and initiator in isopropyl alcohol (IPA) were prepared and applied to ePTFE substrates as follows. Sample conditions utilized for this experiment are summarized in Table 4. Coating solution compositions are shown in % volume for Compound I, and mg/ml for Compound III. Coating solutions for all samples were Compound I/Compound III in IPA. The soak time is the amount of time the substrates were immersed in the coating solution, and the UV time curing is the amount of time the substrate was illuminated with light to couple the coating to substrates.

TABLE 4

| Sample No. | Coating Solution (Compound I/Compound III) | Soak time (minutes) | UV Time Curing |
|---|---|---|---|
| 1 | 10% v/v/0.5 mg/ml | 10 | 3 |
| 2 | 10% v/v/0.5 mg/ml | 10 | 5 |
| 3 | 10% v/v/0.5 mg/ml | 20 | 3 |
| 4 | 10% v/v/0.5 mg/ml | 20 | 5 |
| 5 | 15% v/v/0.5 mg/ml | 10 | 3 |
| 6 | 15% v/v/0.5 mg/ml | 10 | 5 |
| 7 | 15% v/v/0.5 mg/ml | 20 | 3 |
| 8 | 15% v/v/0.5 mg/ml | 20 | 5 |

The ePTFE substrates were soaked in the coating solution, then illuminated wet for the indicated cure times by placing the substrate midway between two opposed ELC-4000 lamps containing 400 watt metal halide/mercury vapor bulbs separated by a distance of 91 cm (36 inches) in a UV chamber. The ePTFE substrates were saturated in the IPA coating solutions in an attempt to overcome hydrophobic nature of the material in order to couple a hydrophilic PEG-based coating on the surface.

Photoderivatized biocompatible agent was coupled to the substrates as follows. Photocollagen, prepared as described in Example 3, was obtained in concentrations of 0.2 mg/ml in 12 mM HCl. The substrates were immersed in the photocollagen solution, allowed to dwell in solution for 1 hour at 4° C., and then illuminated in-solution for 60 seconds per side utilizing a Dymax Blue Wave Spot Cure System (light system commercially available from Dymax Corporation, Torrington, Conn.). The ultraviolet wand of the system was placed at a distance to provide the substrate portions to be coated with approximately 0.5 to 0.25 mW/cm² of light in the wavelength range 330-340 μm. The substrates were gently agitated during the 60 seconds of illumination to ensure that the surfaces were evenly bathed in light.

The substrates were then removed from the photocollagen solution. After removal of the substrates from the photocollagen solution, the substrates were rinsed two times with sterile PBS for thirty minutes per wash, at a temperature of 4° C. The substrates were then soaked 30 minutes in 70% ethanol, then rinsed three times in sterile PBS (1 ml/wash). The substrates were stored in sterile PBS at 4° C.

Example 12

Surface Modification of ePTFE Substrates by Simultaneous Application of Polymeric Matrix Material, Initiator, and Biocompatible Agent Coating solutions containing initiator, polymeric matrix, and biocompatible agent are prepared and applied to ePTFE substrates as follows.

Compounds I, II, and III were prepared as described in previous Examples 1, 2, and 5, respectively. A coating solution containing Compound I/Compound III/Compound II having a concentration of 10-20/0.5-2.0/0.5-2.0% (v/v) in IPA is prepared. ePTFE substrates are then dipped into the coating solutions and subsequently removed at a rate of 0.2-1.0 cm/s. The substrate was then UV cured, either wet or dry, for 3-5 minutes. UV cure is performed by illuminating the substrate for 3 minutes midway between two opposed ELC-4000 lamps containing 400 watt metal halide/mercury vapor bulbs separated by a distance of 91 cm (36 inches).

Optionally, a first priming coat of Compound III is applied prior to the above dip coat. In this method, the ePTFE substrate is first dipped into a solution of Compound III (0.5% v/v in IPA) and illuminated in-solution for 3 minutes (see above conditions). After illumination, the substrate is removed from the solution and rinsed to remove excess initiator solution.

Optionally, the coating solution can include non-photoreactive biocompatible agent. In this case, Compound II is substituted with a non-photoderivatized reagent, such as heparin (or other selected biocompatible agent).

Example 13

Surface Modification of PEBAX Substrates by Simultaneous Application of Polymeric Matrix Material, Initiator, and Biocompatible Agent Six PEBAX rods were coated with aqueous solutions containing polymeric matrix material, initiator, and biocompatible agent as follows. Coating solutions were prepared containing Compound I, Compound IV, and Compound II, prepared as described in Examples 1, 4, and 2, respectively. Concentrations of each compound are summarized in the following Table 5.

The PEBAX rods were dip coated at a speed of 0.5 cm/s and cured wet in a UV chamber for 7 minutes. UV cure is performed by illuminating the substrate for 3 minutes midway between two opposed ELC-4000 lamps containing 400 watt metal halide/mercury vapor bulbs separated by a distance of 91 cm (36 inches).

TABLE 5

| Sample No. | Solution Concentration (Compound I/Compound IV/Compound II) |
|---|---|
| 1, 2 | 10% v/v/10 mg/ml/5 mg/ml |
| 3, 4 | 10/10/10 |
| 5, 6 | 10/10/20 |

Samples 1, 3, and 5 were stained with Toluidine Blue. Staining showed that Sample 1 had the smoothest coating. All samples exhibited coatings that were even and appeared reasonably thick.

Four additional samples were prepared by dipping a PEBAX substrate in aqueous solutions containing Compound I, Compound IV, and Compound II (at concentrations of 10% v/v Compound I, 10 mg/ml Compound IV, and 10 mg/ml Compound II). For these samples, dip speeds and UV cure times were modified as shown in Table 6. UV cure was performed by illuminating the substrates for 3 minutes midway between two opposed ELC-4000 lamps containing 400 watt metal halide/mercury vapor bulbs separated by a distance of 91 cm (36 inches).

TABLE 6

| Sample No. | Dip speed (cm/second) | Cure time (minutes) |
|---|---|---|
| 7 | 0.5 | 5 |
| 8 | 0.5 | 4 |
| 9 | 0.75 | 5 |
| 10 | 0.75 | 4 |

All samples appeared to be adequately cured and coupled to the substrate. These results suggest that cure times can be reduced for the inventive coating compositions for dip speeds of 0.75 cm/s or less.

Example 14

Surface Modification of PEBAX Substrates by Simultaneous Application of Polymeric Matrix Material, and Initiator, and Biocompatible Agent Coating solutions were prepared and applied to PEBAX substrates as follows. Coating solutions included polymeric matrix material, initiator, and biocompatible agent. The coating solutions included Compound I, Compound IV, and either Compound II or native heparin, as described in the following Table 7. PEBAX substrates were immersed in the coating solutions, and UV cure was performed by illuminating the substrate for 3 minutes midway between two opposed ELC-4000 lamps containing 400 watt metal halide/mercury vapor bulbs separated by a distance of 91 cm (36 inches).

TABLE 7

| Sample No. | Coating Composition (% v/v) | Dip speed (cm/second) | Cure time (minutes) |
|---|---|---|---|
| C | 10% Compound I<br>1% Compound IV<br>1% Compound II | 0.75 | 4 |
| D | 10% Compound I<br>1% Compound IV<br>1% Compound II | 0.75 | 4 |
| E | 10% Compound I<br>1% Compound IV | 0.75 | 4 |
| F, G | 10% Compound I<br>1% Compound IV<br>1% native heparin | 0.5 | 4 |
| I | 10% Compound I<br>1% Compound IV<br>1% native heparin | 0.5 | 4 |
| J | 10% Compound I<br>1% Compound IV<br>1% native heparin | 0.75 | 4 |

Visual inspection of the coated samples revealed smooth, conformal coatings for all Samples C through J. This demonstrated that the coating compositions of this Example can be utilized to provide suitable coatings according to the invention.

Regarding samples I and J, the dip coating rate of 0.5 cm/s appeared to give more even coating as compared to a dip coating rate of 0.75 cm/s.

Example 15

Surface Modification of Polyurethane Substrates by Simultaneous Application of Polymeric Matrix Material, Initiator, and Biocompatible Agent Samples of small polyurethane rods with silicon gel plugs at flared tips, flush with tip edge, were coated with various aqueous coating compositions that included polymeric matrix material, initiator, and biocompatible agent, as shown in Table 8.

TABLE 8

| Sample No. | Coating composition | Dip Rate (cm/second) | Cure Time (minutes) |
|---|---|---|---|
| 7 | 10% v/v Compound I<br>10 mg/ml Compound IV<br>10 mg/ml Compound II | 0.2 | 3 |
| 8 | 10% v/v Compound I<br>10 mg/ml Compound IV<br>10 mg/ml Compound II | 0.2 | 3 |
| 9 | 10% v/v Compound I<br>10 mg/ml Compound IV<br>20 mg/ml Compound II | 0.2 | 3 |
| 10 | 10% v/v Compound I<br>10 mg/ml Compound IV<br>10 mg/ml Compound II | 0.2 | 3 |
| 11 | 10% v/v Compound I<br>10 mg/ml Compound IV<br>20 mg/ml Compound II | 0.2 | 3 |

For samples 10 and 11, prior to dipping the solutions in the above-identified coating compositions, the substrates were first immersed in a solution of Compound IV. This "priming" step with the initiator was performed by dipping the substrate in an aqueous solution of Compound IV at a concentration of 5 mg/ml and illuminating the substrate in-solution for 3 minutes midway between two opposed ELC-4000 lamps containing 400 watt metal halide/mercury vapor bulbs separated by a distance of 91 cm (36 inches). The primed substrates were removed from the Compound IV solution, rinsed with distilled water to remove excess coating solution, then dipped in the coating compositions indicated in Table 8.

Samples 7 and 9 were stained with Toluidine Blue. Staining showed that both samples had thin, even coatings which stained well.

Visual inspection of samples 10 and 11 revealed a similar appearance to sample 8; i.e., the dip coating appeared to sheet as well over a coating of Compound IV as it did over a layer of coating solution composed of Compound I, Compound IV, and Compound II. No solids were formed in the coating solution during illumination. For samples 7 through 9, an in-solution illumination with coating compositions composed of Compound I, Compound IV, and Compound II showed formation of a mostly-solid gel in the test tubes, even at UV illumination times of 1 minute or less. For samples 10 and 11, however, the priming solution of Compound IV alone remained liquid during in-solution illumination step, allowing for a priming layer of Compound IV to be applied to the substrate in a suitable manner.

Example 16

Heparin Activity of Coated PEBAX Substrates

PEBAX rods were coated with various coating solutions and assayed to determine the biocompatible agent activity of coated substrates as follows. For this Example, the following coating solutions were prepared:

| Coating A: | Compound I | (10% v/v) |
| | Compound IV | (10 mg/ml) |
| | Compound II | (10 mg/ml) |
| Coating B: | Compound I | (10% v/v) |
| | Compound IV | (10 mg/ml) |
| | Heparin | (10 mg/ml) |
| Coating C: | Compound I | (10% v/v) |
| | Compound IV | (10 mg/ml) |

A first set of PEBAX rods were coated with aqueous solutions of Coating A, a second set were coated with aqueous solutions of Coating B, and a third set of PEBAX rods were coated with aqueous solutions of Coating C. All PEBAX rods were dip coated at a speed of 0.5 cm/s and cured wet in a UV chamber for 7 minutes. UV cure was performed by illuminating the substrates midway between two opposed ELC-4000 lamps containing 400 watt metal halide/mercury vapor bulbs separated by a distance of 91 cm (36 inches).

All PEBAX rods were subjected to the Heparin Activity Assay described herein. Results are shown in Table 9.

TABLE 9

| Coating Composition | Activity $MU/cm^2$ | mean | SD |
|---|---|---|---|
| A | 27 | 23 | 8 |
| | 14 | | |
| | 30 | | |
| B | 12 | 12 | 1 |
| | 12 | | |
| | 14 | | |
| C | 6 | 6 | 0 |
| | 6 | | |
| | 6 | | |

Results indicate that higher heparin activity is observed when a photoderivatized biocompatible agent (in this case, Compound II) is utilized as compared to a non-derivatized biocompatible agent (in this case, heparin). Results also indicated that samples utilizing a coating solution of Compound I/Compound IV produced activities similar to background activities of uncoated PEBAX controls (results not shown). In other words, no heparin activity was seen in those samples that did not include any heparin, either photoheparin or non-derivatized heparin. Thus, heparin activity seen in these assays was attributable to heparin present in the coating compositions applied to the PEBAX substrates.

Example 17

Surface Modification of PEBAX Substrates by Simultaneous Application of Polymeric Matrix Material, Initiator, and Biocompatible Agent Coating compositions of various components were provided on PEBAX substrates to determine the effect of priming a substrate surface with initiator.

Coating compositions utilized in this Example are summarized in Table 10.

TABLE 10

| Sample No. | Priming | Coating Composition | Photo- or nonderivatized biocompatible agent |
|---|---|---|---|
| W | 0.5% Compound IV | 10-20% Compound I 0.5-2.0% Compound IV 0.5-2.0% Compound II | Photoheparin |
| X | None | 10-20% Compound I 0.5-2.0% Compound IV 0.5-2.0% Compound II | Photoheparin |
| Y | 0.5% Compound IV | 10-20% Compound I 0.5-2.0% Compound IV 0.5-2.0% Heparin | Non-photo heparin (heparin macromer or sodium heparin) |
| Z | None | 10-20% Compound I 0.5-2.0% Compound III 0.5-2.0% Heparin | Non-photo heparin (heparin macromer or sodium heparin) |

When priming was performed (Samples W and Y), the substrates were submerged in an aqueous solution of initiator at the indicated concentrations and illuminated in-solution for 3 minutes. The substrates were then rinsed to remove unbound initiator.

After priming (if done), the substrates were submerged in the Coating Composition (Table 10), with a coating rate of 0.2 to 1.0 cm/s and UV cured, either wet or dry, for 3-5 minutes.

For all UV cure in this Example, cure was performed by illuminating the substrates midway between two opposed ELC-4000 lamps containing 400 watt metal halide/mercury vapor bulbs separated by a distance of 91 cm (36 inches).

Results indicated that priming with initiator is helpful, but not required, for application of the coating solutions containing polymeric matrix material, initiator, and biocompatible agent. Both single and multiple topcoats were successfully applied by this method, each coat receiving the same approximate cure time.

Example 18

Application of Collagen Macromer to PEBAX Substrates

A collagen macromer was prepared as follows. Bovine tendon collagen, Type I, was obtained from ReGen Corp. The collagen (0.5 grams) was dissolved in 20 ml dry formamide by incubating for 20 hours on an orbital shaker at 37° C. TEA was added with stirring, in an amount of 1.0 gram (9.8 mmole), and the reaction was equilibrated for 60 minutes in an ice water bath. Acryloyl chloride was added in 0.25 gram aliquots (rate of 1 aliquot per minute) with stirring, for a total amount of 1.0 gram (11 mmole) acryloyl chloride added. After the final addition, the solution was stirred in an ice water bath for 2 hours. The reaction was removed from the ice water bath and stirring was continued at room temperature for 18 hours. The product, collagen containing polymerizable groups (identified as "collagen macromer" in the Table 11 below), was purified by dialysis against deionized water using 6-8K MWCO dialysis tubing, and isolated by lyophilization.

PEBAX rods were obtained and subjected to coating with compositions summarized in the following Table 11.

TABLE 11

| Sample No. | Priming solution | Coating Composition |
|---|---|---|
| 0 (control) | None | None |
| 1 | Compound IV | Collagen macromer (20 mg/ml) |
| 2 | Compound IV | Collagen macromer (20 mg/ml) |
| 3 | Compound IV | Collagen macromer (30 mg/ml) |
| 4 | Compound IV | Collagen macromer 30 mg/ml |
| 5 | Compound IV | Collagen macromer 20 mg/ml; Photocollagen (200 µg/ml) |
| 6 | Compound IV | Collagen macromer 30 mg/ml; Photocollagen (200 µg/ml) |

For all samples, priming was done by immersing the PEBAX substrates in a solution of Compound IV in water at a concentration of 5 mg/ml. For all samples and coating steps in this Example, UV cure was performed by illuminating the substrates for 3 minutes in-solution, midway between two opposed ELC-4000 lamps containing 400 watt metal halide/mercury vapor bulbs separated by a distance of 91 cm (36 inches). Samples were rinsed to remove unbound Compound IV.

Next, samples were dipped in solutions of collagen macromer at the concentrations identified in Table 11 in water. Coating rates were as follows 0.75 cm/s for Samples 1-3 and 5-6; 1.0 cm/s for Sample 4. Following the collagen macromer coating step, the Samples 2-6 were illuminated, wet, for 5 minutes. Sample 1 was allowed to air dry subsequent to the collagen macromer coating step, then illuminated dry for 3 minutes.

Samples 5 and 6 were then subjected to an additional coating of photocollagen (prepared as described in Example 3) as follows. Solutions of photocollagen at concentration of 200 µg/ml in water were prepared. Substrates were dipped into the photocollagen solutions at a rate of 0.75 cm/s. The substrates were then illuminated, wet, for 5 minutes.

Completed samples were subject to FITC staining to determine coating efficacy. For FITC staining, 10 mg FITC (Isomer I, Molecular Probes F-1906) was solubilized in 2 ml of 100% ethanol. The solubilized FITC was stored at −20° C. until use (concentration=5 mg/ml). Upon use, the FITC was diluted 1:20 in 0.1 M borate buffer, pH 9.0 to 250 µg/ml. Samples were immersed in the FITC stain for 1 hour in the dark at room temperature. After staining, the samples were removed from the stain, rinsed four times with borate buffer, followed by a rinse with water, then air dried. Samples were observed by fluorescent microscopy.

Results indicated that all coated samples stained strongly and appeared uniform and consistent from one sample to the next. Subsequent contrast enhancement revealed minor inconsistencies in several of the coatings. Coating 2, with collagen macromer at 20 mg/ml illuminated wet for 5 minutes, appeared to stain less intensely than macromer coatings illuminated dry, at higher concentrations, and/or with an additional topcoat of photocollagen.

Example 19

Surface Modification of Silicone Substrates by Sequential Application of Photopolyvinylpyrrolidone, Polymeric Matrix Material with Nonpolymeric Initiator

Compound V, an acetylated photo-PVP is prepared by the copolymerization of 1-vinyl-2-pyrollidone and N-(3-aminopropyl)methacrylamide. The copolymers are derivatized with an acyl chloride (such as, for example, 4-benzoylbenzoyl chloride) under Schotten-Baumann conditions and the unreacted amines of the polymer are acetylated using acetic anhydride to give an acetylated photo-PVP. That is, the acyl chloride reacts with some of the amino groups of the N-(3-aminopropyl) moiety of the copolymer, resulting in the attachment of the aryl ketone to the polymer. The liberated hydrochloric acid is neutralized with an aqueous base solution. The structure of the product is shown as Compound V herein.

A silicone substrate is first prepared with a thin layer of Compound V by the following method. A solution of Compound V is prepared at a concentration of 5 mg/ml in deionized water. The substrate is immersed in this coating solution and illuminated in-solution 3 minutes midway between two opposed ELC-4000 lamps containing 400 watt metal halide/mercury vapor bulbs separated by a distance of 91 cm (36 inches). Once illumination is complete, the substrate is removed from the solution and rinsed in deionized water to remove any unbound Compound V. This process leaves a thin "tie layer" of Compound V on the substrate surface. The treated material is allowed to air dry before proceeding to the next step.

Once dry, the substrate is then submerged in a solution containing both Compound I and Compound IV (at concentrations of 10 and 1% v/v respectively, in deionized water), and removed by lifting at a rate of 0.2 to 1.0 cm/s. The coated substrate is then illuminated while still wet for 5 to 7 minutes.

Example 20

Preparation of Biocompatible Agent including Polymerizable Groups [Collagen Macromer] (Compound VI)

A mixture of Types I and III collagen was obtained from Semed-S, Kensey-Nash Corp. The collagen (1.0 grams) was dissolved in 50 mls of 0.01N HCl. When dissolved, 1.25 grams triethylamine (12.4 moles) was added to the reaction mixture. One gram of acryloyl chloride (11.0 mmoles) dissolved in one milliliter of methylene chloride was added to the reaction vessel and the mixture was stirred for 20 hours at room temperature.

The reaction mixture was dialyzed exhaustively against diH$_2$O, and the product (Compound VI) isolated by lyophilization.

Example 21

Surface Modification of PEBAX Substrates by Sequential Application of Initiator, Polymeric Matrix Material, and Photoderivatized Biocompatible Agent

In this Example, a polymerization initiator containing photoreactive groups and an overall positive charge was utilized. The polymerization initiator ethylenebis(4-benzoylbenzyldiemthlammonium) dibromide (Compound VII) was prepared as follows.

N,N,N',N'-Tetramethylethylenediamine, 6 g (51.7 mmol), was dissolved in 225 ml of chloroform with stirring. 4-Bromomethylbenzophenone, 29.15 g (106.0 mmol), was added as a solid and the reaction mixture was stirred at room temperature for 72 hours. After this time, the resulting solid was isolated by filtration and the white solid was rinsed with cold chloroform. The residual solvent was removed under vacuum and 34.4 g of solid were isolated for a 99.7% yield, melting point 281-220° C. Analysis on an NMR spectrometer was consistent with the desired product: $^1$H NMR (DMSO-d$_6$) aromatic protons 7.20-7.80 (m. 18H), benzylic methylenes 4.80 (br. s. 4H), amine methylenes 4.15 (br. s. 4H), and methyls 3.15 (br. s. 12H). See Example 2, U.S. Pat. No. 5,714,360 (Swan et al.).

For the samples in this Example 21, the following conditions apply to immersion and UV cure steps. Samples were immersed into coating solutions and subsequently withdrawn at a rate of 0.25 cm/second to coat the desired length of the device substrate. Unless indicated otherwise, coating was applied to the entire length of the substrate. UV cure was performed by illuminating the substrate for 3 minutes midway between two opposed ELC-4000 lamps containing 400-watt metal halide/mercury vapor bulbs separated by a distance of 91 cm (36 inches).

PEBAX substrates were first primed with nonpolymeric initiator and polymeric matrix material as follows. Twenty (20) PEBAX rods were obtained. A coating solution including Compound V (10% v/v, prepared as described in Example 19), PVP K90/K30 (20/40% v/v), and Compound IV (1.5 mg/ml, prepared as described in Example 4) was prepared in 15% IPA/85% water. PEBAX substrates were immersed in the coating solution and subsequently withdrawn at a rate of 0.25 cm/second, and allowed to air dry for approximately 10 minutes or more (until sufficiently dried). The samples were then cured wet under the UV cure conditions described above. The coated substrates contained a hydrophilic coating layer at the surface. The twenty coated samples were then divided into three groups and processed as follows:

Group I: Ten (10) samples were immersed in a coating solution containing Compound VI (prepared as described in Example 20) and Compound VII (10/0.8 mg/ml in water). The bottom half of the PEBAX substrates was immersed in the coating solution. The coatings were cured wet 3 minutes in a UV chamber. Of these ten samples, five were subjected to friction testing and five were evaluated by immunofluorescence assay. The hydrophilic-only coating area of each sample was used as a control to determine background fluorescence; exposure time on the fluoroscope was adjusted to identify fluorescence generated specifically by the collagen top coat.

Group II: Five (5) samples were immersed in a coating solution containing Compound VI (prepared as described in Example 20) and Compound VII (10/0.8 mg/ml in water). In this Group II, the entire length of the PEBAX samples were immersed in coating solution. The coatings were cured wet. All five samples of this Group II were subjected to friction testing, and then evaluated by immunofluorescence assay.

Group III: Five (5) samples were evaluated with no top coat to check the integrity of the hydrophilic base coat.

For friction testing, samples were friction tested with a pinch force of approximately 300 g for a total of 15 cycles per sample, and then stained with Congo Red. Friction testing was performed to assess lubricity and tenacity of the coatings on the samples, as well as the difference (if any) among samples coated with hydrophilic coating only (PVP/initiator base coat only) versus samples coated with biocompatible agent top coats (collagen macromer with nonpolymeric initiator).

Coated substrates were evaluated by a horizontal sled style friction test method (modified ASTM D-1894, as described below). Silicone Pads (7 mm diameter) were hydrated and then wrapped around a 200 gram stainless steel sled. The silicone pad was clipped together tightly on the opposite side of the sled. The sled with rotatable arm was then attached to a 300 gram Chatillon Digital Force Gauge (DGGH, 300×0.1) with computer interface. The testing surface was mounted on a 22.5 inch positioning rail table with micro-stepper motor control (Compumotor SX6 Indexer/Drive).

Coated substrates were hydrated in deionized water and clamped onto the test surface 1 inch (or approximately 2.5 cm) apart. The hydrated Silicone pad (jaw force set at 300 g) moved at 0.5 cm/sec over a 5 cm section for 15 push/pull cycles, and force measurements were taken for the cycles.

Figure 3:
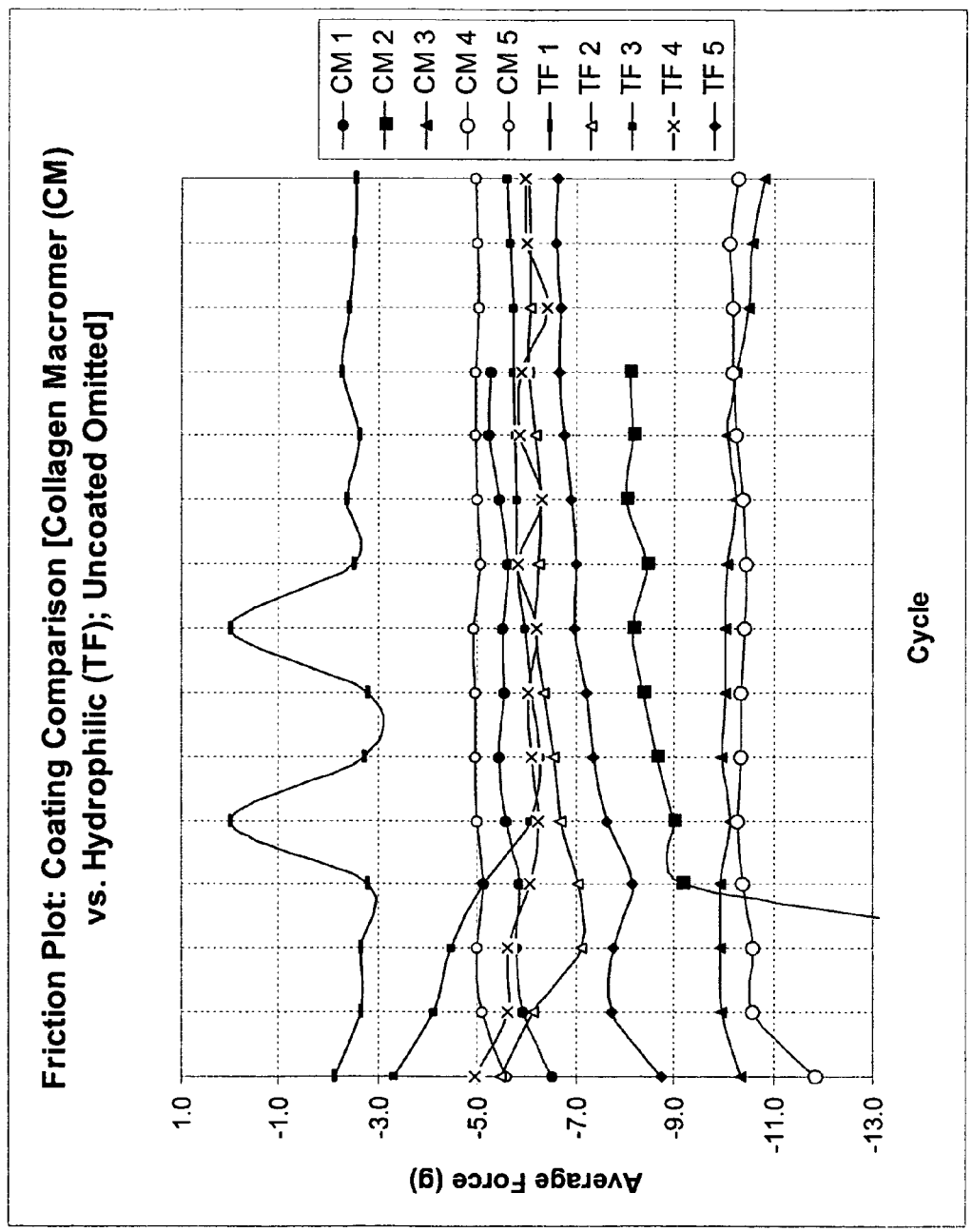
FIG. 3 is a graph illustrating the relationship of average frictional force (g, Y-axis) and cycle number (X-axis) of coated medical articles made in accordance with one embodiment of the invention.

Results of friction testing are summarized in the table and graphs of FIGS. 1-3. In the graphs, data is plotted as average force per cycle of testing. Negative frictional forces indicated a downward force direction, opposing the upward motion of the sample. Force data did not appear to indicate a significant increase in frictional force as a result of collagen top coat application, as hydrophilic base coat samples (TF) and hydrophilic+collagen (CM) samples generated similar frictional forces during testing. Moreover, the hydrophilic base coat only (TF) and hydrophilic+collagen (CM) provided coatings having excellent durability, as the grams of force remained relatively constant for the 15 cycles, indicating a durable coating. A significant difference in lubricity was observed between uncoated samples and coated samples (both hydrophilic base coat only, TF, and hydrophilic+collagen, CM).

For immunofluorescence assay, the samples were viewed with a fluorescence microscope.

Samples were blocked with 1.5% BSA in TBST for 20 minutes at room temperature on an orbital shaker. The samples were then rinsed in Dulbecco's cation free phosphate buffered saline (DCF-PBS). Samples were incubated with collagen I antibody (Rockland, 600-401-103-0.1) diluted to 1:200 with DCF-PBS at room temperature for one hour on an orbital shaker. The samples were then washed three times in DCF-PBS. Washed samples were then incubated with anti-rabbit Texas Red antibody (Rockland, 611-1902) diluted to 1:300 with DCF-PBS at room temperature for one hour while shaking. After incubation, samples were washed three times with DCF-PBS. Samples were then imaged with the fluorescence microscope. Settings on the fluoroscope were adjusted to minimize background fluorescence from the hydrophilic base coat in order to identify the contribution from the collagen macromer top coat.

Overall, results from immunofluorescent staining of samples subjected to friction testing did not reveal significant coating removal. Results showed that collagen top coat coverage was achieved across the entire surface that was immersed in coating solution. For Group III, results indicated that the hydrophilic base coat was durably retained at the surface of the substrates.

For samples in Group I, in which half of the PEBAX substrates were coated with collagen macromer, immunofluorescent staining demonstrated that a distinct border between the hydrophilic only area and hydrophilic plus collagen macromer coating could be achieved. A distinct border was present, with the collagen-coated area providing a brighter fluorescent signal for all samples.

For samples in Group II, in which the entire length of the PEBAX substrates were coated with collagen macromer, immunofluorescent staining demonstrated that friction testing did not remove a significant amount of the collagen coating. No wear patters were visible as a result of the friction testing.

Example 22

Multifunctional Device Including ePTFE and Polyurethane Material Portions

An assembled medical article having portions fabricated of ePTFE and portions fabricated of polyurethane (containing a silicone tip) was provided with coatings according to some embodiments of the invention as follows. Efficacy of different coating types by a qualitative analysis of surface coverage, as well as a quantitative measurement of biocompatible agent activity, was compared among the samples.

Samples for this example are summarized in Table 12 below. Solvents were aqueous (water), isopropyl alcohol (IPA) or hydrochloric acid (HCl).

TABLE 12

| Sample | Substrate Material | Base Coat | Top Coat |
|---|---|---|---|
| 1, 4 | Polyurethane/silicone tip | 10% v/v Compound I<br>10 mg/ml Compound IV<br>20 mg/ml Compound II<br>in water | 10% v/v Compound I<br>10 mg/ml Compound IV<br>10 mg/ml Compound II<br>in water |
| 2, 5 | Polyurethane/silicone tip | 5 mg/ml Compound IV<br>in water | 10% v/v Compound I<br>10 mg/ml Compound IV<br>10 mg/ml Compound II<br>in water |
| 3, 6 | Polyurethane/silicone tip | 5 mg/ml Compound IV<br>in water | 10% v/v Compound I<br>10 mg/ml Compound IV<br>20 mg/ml Compound II<br>in water |
| 7 | ePTFE | (none) | (none) |
| 8 | ePTFE | 15% v/v Compound I<br>0.5 mg/ml Compound III<br>in IPA | (none) |
| 9 | ePTFE | 5 mg/ml Compound V<br>in water | 200 µg/ml Photocollagen (Example 3)<br>in 12 mM HCl |
| 10 | ePTFE | 5 mg/ml Compound V<br>in water | 30 mg/ml Compound VI<br>in water |
| 11 | ePTFE | 15% Compound I<br>0.5 mg/ml Compound III<br>in IPA | 200 µg/ml Photocollagen (Example 3)<br>in 12 mM HCl |
| 12 | ePTFE | 15% Compound I<br>0.5 mg/ml Compound III<br>in IPA | 30 mg/ml Compound VI<br>in water |

Substrates were immersed in the coating solution identified as "Base Coat" in Table 12 and were illuminated in-solution for determined illumination times midway between two opposed ELC-4000 lamps containing 400-watt metal halide/mercury vapor bulbs separated by a distance of 91 centimeters (36 inches). Several samples were soaked in the coating solution prior to in-solution illumination. Illumination conditions for samples is summarized in Table 13.

TABLE 13

| Sample | Base Coat |
|---|---|
| 1, 4 | In solution illumination 1.5 minutes |
| 2, 5 | In solution illumination 3 minutes |
| 3, 6 | In solution illumination 3 minutes |
| 7 | (none) |

TABLE 13-continued

| Sample | Base Coat |
|---|---|
| 8 | Soak in coating solution 5 minutes, illuminate 4 minutes |
| 9 | In solution illumination 3 minutes |
| 10 | In solution illumination 3 minutes |
| 11 | Soak in coating solution 5 minutes, illuminate 4 minutes |
| 12 | Soak in coating solution 5 minutes, illuminate 4 minutes |

The resulting substrates included a base coat of the coating composition. The substrates were then immersed in the coating solutions indicated as "Top Coat" in Table 12. For Samples 1-6, substrates were immersed in the coating solution and subsequently withdrawn at a rate of 0.20 cm/second, followed by illumination (wet) for 3 minutes. For Samples 9-12, substrates were immersed in the coating solution and subsequently withdrawn at a rate of 0.25 cm/second, then illuminated wet for 3 minutes. For all Samples at this stage, substrates were illuminated for determined illumination times midway between two opposed ELC-4000 lamps containing 400-watt metal halide/mercury vapor bulbs separated by a distance of 91 centimeters (36 inches).

Coated samples were evaluated as follows. Polyurethane portions were stained, inspected under a microscope and assayed for heparin activity; ePTFE portions were subjected to fluorescent imaging (FITC) analysis. Samples 1-3 were stained with Toluidine Blue to determine coating thickness and consistency. All samples stained well, with a uniform color and texture. After staining, samples were placed under an optical microscope (60×) for visual inspection, to determine extent of coating on the silicone gel surface. This inspection revealed that recessed areas of the device tips appeared to be evenly coated, with a thin layer of coating contacting the silicone gel surface itself.

Samples 4-6 were assayed for heparin activity by UV/VIS according to the Heparin Activity Assay described herein; Table 14 summarizes results.

TABLE 14

| | Heparin activity. | | |
|---|---|---|---|
| Sample | ABS 405 um | MU | MU/cm$^2$ |
| 4 | 0.754 | 5 | 17 |
| 5 | 0.694 | 9 | 30 |
| 6 | 0.679 | 10 | 33 |

Results of the heparin activity assay showed that heparin activity levels varied depending upon the substrate, with some substrates producing relatively more or less background noise in the analysis. However, for these experiments, an activity level of 15-20 or above was considered acceptable.

Results indicated that the polyurethane portions of the samples stained well and exhibited acceptable heparin activity. The stained coating on the device tip (to an approximate distance of 5 mm from the tip), where the coatings were applied, was examined under a microscope and appeared to the sufficiently thick and even. Coatings appeared to be approximately 20μ in thickness or less. From a heparin activity standpoint, utilization of a (relatively) higher concentration of heparin in the top coat did not appear to provide a significantly higher heparin activity in the final coating.

Samples 7-12 were subjected to FITC imaging. For Sample 7 (uncoated), and 9-10 (base coat of photo-PVP and top coat of collagen), no fluorescence was observed. The absence of signal for Samples 9 and 10 is believed to be a result of the hydrophobic nature of the ePTFE substrate, and is thus is likely to work with a different solvent (nonaqueous), as done for Samples 11-12. Fluorescence was observed for Samples 8 and 11-12, with Samples 11-12 providing a strong and even fluorescent signal.

Example 23

Surface Modification of Polycarbonate Substrates

Polycarbonate substrates were coated with biocompatible agent to reduce platelet attachment to the substrates as follows.

Polycarbonate substrates were cleaned with IPA and air dried. The cleaned substrates were then immersed in a coating solution containing Compound V (prepared as described in Example 19) and Compound III (prepared as described in Example 5) (10/0.5 mg/ml in IPA) and subsequently withdrawn as follows:
Group I: 0.2 cm/second
Group II: 0.15 cm/second
Group III: 0.25 cm/second The coated samples were then suspended vertically and illuminated for 3 minutes. UV cure was performed by illuminating the substrate for 3 minutes midway between two opposed ELC-4000 lamps containing 400 watt metal halide/mercury vapor bulbs separated by a distance of 91 cm (36 inches). Samples were rotated during illumination. The substrates were then cooled.

The coated samples were then placed in IPA extraction baths along with two uncoated controls. Bath samples (approximately 60 ml each) were then submitted for analytical testing to quantify extraction of leached substances from the coating surface. Two extraction processes were utilized: one sample from each group and one uncoated sample were sonicated in an EPA bath for 30 minutes at room temperature; one sample from Group I was placed, with one uncoated control, in an IPA bath (100% IPA) and soaked for 24 hours at 37° C. After soaking, the samples were removed from the IPA. A UV/Vis spectrophotometer was used to determine the concentration of the drug in the IPA solution that previously contained the sample with the coating composition (detection wavelength 265 μm). Analytical results indicated a significantly higher level of leached coating with the soaked samples.

Example 24

Surface Modification of Internal Surface of PEBAX Tubing

The internal surface of clear PEBAX tubing was provided with a coating containing photoreactive macromer, Compound IV and Compound III as follows.

The photoreactive macromer utilized was non-acetylated photo-PVP (prepared as described in U.S. Pat. No. 5,637,460, see Example 4). Generally, the photo-PVP was prepared by copolymerization of 1-vinyl-2-pyrrolidone and N-(3-aminopropyl)methacrylamide (APMA), followed by photoderivatization of the polymer using an acyl chloride (such as, for example, 4-benzoylbenzoyl chloride) under Schotten-Baumann conditions. The acyl chloride reacts with some of the amino groups of the N-(3-aminopropyl) moiety of the copolymer, resulting in the attachment of the aryl ketone to the polymer. The liberated hydrochloric acid is neutralized with an aqueous base solution. The polymer is referred to as Compound VI herein.

A coating solution including Compound IV (15% v/v, prepared as described in Example 4), PVP K90™/K30™ (20/40% v/v), Compound IV (2.5 mg/ml, prepared as described in Example 4), and Compound III (0.075 mg/ml, prepared as described in Example 5) was prepared in 60% IPA/40% water. PEBAX tubing was cleaned by flushing the internal diameter (hereafter "ID") with IPA, then drying with a stream of nitrogen.

The coating solution was sucked into the ID of the tubing using a syringe. The solution was allowed to dwell within the ID for approximately 60 seconds, then the syringe was removed and the solution drained by gravity. The tube was attached to a nitrogen supply and the ID was blown dry.

The coated tubing was suspended in a UV chamber for cure. UV cure was performed by illuminating the substrate for 3 minutes midway between two opposed ELC-4000 lamps containing 400-watt metal halide/mercury vapor bulbs separated by a distance of 91 cm (36 inches).

The UV cured ID coating was evaluated for uniformity by injecting a 0.35% Congo Red stain solution (in water) into the tubing for 60-120 seconds, and then removing the stain solution and rinsing the ID with water. Congo Red selectively stains the coating, and not the tubing material itself, allowing qualitative assessment of coating coverage. The stain was observed to be uniform with no patches or gaps. Several 20 ml volumes of water were passed through the tube with no loss of stain (coating), indicating at least moderate durability of the coating.

Next, a length of LDPE/polyvinyl acetate rod (only slightly smaller outer diameter than the ID of the coated tube) was inserted through the coated and hydrated ID and pushed and pulled through multiple times. This confirmed both the durability of the coating (no loss of stain) and the lubricity, since the LDPE rod would become stuck in an uncoated section of tubing and could be passed through the coated section of tubing multiple passes with only moderate force necessary.

Slightly smaller outer diameter tubing of a different plastic type was also passed through coated and uncoated PEBAX tubing that had 3-4 bends in it (30-40 degree bends) to mimic a tortuous path. The smaller tubing was manually pushed and pulled through the PEBAX tubing. It was observed that coated ID samples allowed the test tubing to move more easily through through the ID, relative to uncoated ID samples, illustrating a lubricious effect of the coatings on the ID of samples.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

We claim:

1. A medical article comprising:
   (a) a body member;
   (b) a first biocompatible coating at a first surface portion of the body member, the first biocompatible coating comprising polymerization initiator and a first biocompatible agent, the first biocompatible agent including one or more reactive groups, one or more polymerizable groups, or a combination of one or more reactive groups and one or more polymerizable groups; and
   (c) a second biocompatible coating at a second surface portion of the body member, the second biocompatible coating comprising polymerization initiator and a second biocompatible agent, the second biocompatible agent including one or more reactive groups, one or more polymerizable groups, or a combination of one or more reactive groups and one or more polymerizable groups,
   wherein the first biocompatible agent and second biocompatible agent are covalently and nonreleasably immobilized in their respective coatings at respective surface portions and are selected to provide different biocompatible functions when the surface portions are in contact with bodily fluids of a patient;
   wherein the first surface portion and the second surface portion are distinct portions on the body member of the medical article; and
   wherein the first biocompatible agent and the second biocompatible agent are different biocompatible agents thereby providing different biocompatible functions to the first and the second surface portions of the body member of the article.

2. The article according to claim 1 wherein the medical article is an implantable medical device.

3. The article according to claim 2 wherein the implantable medical device is an implantable sensor catheter, transmyocardial sensor or sensor catheter, osteochondral fixative, embolization coil, artificial valve, stented graft, stented valve, valved graft, transdermal access device or shunt, or tunneled access catheter or shunt.

4. The article according to claim 1 wherein the medical article is an external medical article selected from the group consisting of blood cell separator devices, blood cell concentrator devices, blood cell counter devices, hemodialysis blood filtration devices, blood oxygenation devices, blood processing devices and blood diagnostic system systems.

5. The article according to claim 1 wherein the first biocompatible coating, the second biocompatible coating, or both the first biocompatible coating and the second biocompatible coating further comprise a macromer that includes a polymeric backbone and polymerizable groups.

6. The article according to claim 5 wherein the polymeric backbone is selected from polyvinylpyrrolidone, polyethylene glycol, polyacrylamide, polyvinyl alcohol.

7. The article according to claim 5 wherein the polymeric backbone is selected from synthetic polymers formed from monomers comprising methyl methacrylate, butyl methacrylate, dimethyl siloxanes, or combinations of these.

8. The article according to claim 5 wherein the polymerizable groups are independently selected for each surface portion and are selected from vinyl groups, (meth)acrylamide groups, and (meth or eth)acrylate groups.

9. The article according to claim 1 wherein the first surface portion and the second surface portion of the medical article are fabricated from different materials.

10. The article according to claim 1 wherein the first biocompatible agent is a thrombin inhibitor and the second biocompatible agent is an adhesion promoter.

11. The article according to claim 10 wherein the thrombin inhibitor is selected from heparin, heparin derivatives, sodium heparin, low molecular weight heparin, high affinity heparin, low affinity heparin, hirudin, lysine, prostaglandins, argatroban, forskolin, vapiprost, prostacyclin and prostacyclin analogs, D-phenylalanyl-L-propyl-L-arginine chloromethylketone-thrombin, dipyridamole, glycoprotein IIb/IIIa platelet membrane receptor antibody, coprotein IIb/IIIa platelet membrane receptor antibody, recombinant hirudin, thrombin inhibitor, chondroitin sulfate, modified dextran, albumin, streptokinase, tissue plasminogen activator, urokinase, and nitric oxide inhibitors.

12. The article according to claim 10 wherein the adhesion promoter is selected from fibronectin, laminin, collagen, elastin, vitronectin, tenascin, fibrinogen, thrombospondin, osteopontin, von Willebrand Factor, bone sialoprotein, hyaluronic acid, chitosan, methyl cellulose.

13. The article according to claim 1 wherein the polymerization initiator of the first biocompatible coating, the second biocompatible coating, or both the first biocompatible coating and second biocompatible coating, is pendent from a polymeric backbone.

14. The article according to claim 13 wherein the polymerization initiator is independently selected for each surface portion and the polymeric backbone is selected from the group consisting of polyvinylpyrrolidone, polyethylene glycol, polysaccharides, and polyacrylamides.

15. The article according to claim 13 wherein the polymerization initiator is independently selected for each surface portion and is selected from 4-benzoylbenzoic acid, [9-oxo-2-thioxanthanyl)-oxy]acetic acid, 2-hydroxy thioxanthone, vinyloxymethylbenzoin methyl ether, ethyl eosin, acetophenone, thioxanthone, benzophenone, and camphorquinone.

16. The article according to claim 13 wherein the polymerization initiator is independently selected for each surface portion and is selected from the group consisting of 4,4'-azobis(4-cyanopentanoic acid), 2,2-azobis[2-(2-imidazon-2-yl)propane]dihydrochloride, and benzoyl peroxide.

17. The article according to claim 1 wherein the polymerization initiator of the first biocompatible coating, the second biocompatible coating, or both the first biocompatible coating and second biocompatible coating, is independently selected for each surface portion and is selected from the group consisting of a tetrakis (4-benzoylbenzyl ether) of pentaerythritol and a tetrakis (4-benzoylbenzoate ester) of pentaerythritol.

18. The article according to claim 1 wherein in the polymerization initiator of the first biocompatible coating, the second biocompatible coating, or both the first biocompatible coating and the second biocompatible coating, is independently selected for each surface portion and is selected from the group consisting of 4,5-bis(4-benzoylphenylmethyleneoxy)benzene-1,3-disulfonic acid dipotassium salt, 4,5-bis(4-benzoylphenylmethyleneoxy)benzene-1,3-disulfonic acid disodium salt, 2,5-bis-(4-benzoylphenylmethyleneoxy) benzene-1,4-disulfonic acid dipotassium salt, 2,5-bis-(4-benzoylphenylmethyleneoxy)benzene-1,4-disulfonic acid disodium salt, 2,5-bis(4-benzoylphenylmethyleneoxy)benzene-1-disulfonic acid monopotassium salt, 2,5-bis(4-benzoylphenylmethyleneoxy)benzene-1-disulfonic acid monosodium salt, and combinations of any of these.

19. The article according to claim 1 wherein the first biocompatible agent includes one or more photoreactive groups.

20. The article according to claim 1 wherein the biocompatible agent of the first biocompatible coating, the second biocompatible coating, or both the first biocompatible coating and the second biocompatible coating, includes one or more polymerizable groups selected from vinyl groups, (meth)acrylamide groups, and (meth or eth)acrylate groups.

21. The article according to claim 1 wherein the second biocompatible agent includes one or more photoreactive groups.

22. A method for providing two or more functional surface portions on a body member of a medical article, the method comprising steps of:

(a) disposing a first composition at a first surface portion on the body member of the medical article, the first composition comprising polymerization initiator and a first biocompatible agent, the first biocompatible agent including one or more reactive groups, one or more polymerizable groups, or a combination of one or more reactive groups and one or more polymerizable groups;

(b) activating the polymerization initiator, reactive groups, or a combination thereof, to form a biocompatible coating layer at the first surface portion;

(c) disposing a second composition at a second surface portion on the body member of the medical article, the second composition comprising polymerization initiator and a second biocompatible agent, the second biocompatible agent including one or more reactive groups, one or more polymerizable groups, or a combination of one or more reactive groups and one or more polymerizable groups; and (d) activating the polymerization initiator, reactive groups, or a combination thereof, to form a biocompatible coating layer at the second surface portion, wherein the first biocompatible agent and the second biocompatible agent are immobilized at respective surface portions according to steps (b) and (d) and are selected to provide different biocompatible functions when the surface portions become covalently and non-releasably in contact with bodily fluids of a patient wherein the first surface portion and the second surface portion are distinct portions on the body member of the medical article; and wherein the first biocompatible agent and the second biocompatible agent are different biocompatible agents thereby providing different biocompatible functions to the first and the second surface portions of the body member of the article.

23. The method according to claim 22 wherein the medical article is an implantable medical device.

24. The method according to claim 22 wherein the first composition, the second composition, or both the first composition and the second composition further comprise a macromer that includes a polymeric backbone and polymerizable groups.

25. The method according to claim 22 wherein the first biocompatible agent is a thrombin inhibitor and the second biocompatible agent is an adhesion promoter.

26. The method according to claim 22 wherein in the disposing step (a), disposing step (c), or both the steps (a) and (c), the polymerization initiator is pendent from a polymeric backbone.

27. The method according to claim 26 wherein the polymerization initiator is independently selected for each surface portion and the polymeric backbone is selected from the group consisting of polyvinylpyrrolidone, polyethylene glycol, polysaccharides, and polyacrylamides.

28. The method according to claim 26 wherein the polymerization initiator is independently selected for each surface portion and is selected from the group consisting of 4-benzoylbenzoic acid, [9-oxo-2-thioxanthanyl)-oxy]acetic acid, 2-hydroxy thioxanthone, vinyloxymethylbenzoin methyl ether, ethyl eosin, acetophenone derivatives, thioxanthone, benzophenone, and camphorquinone.

29. The method according to claim 26 wherein the polymerization initiator is independently selected for each surface portion and is selected from the group consisting of 4,4'-azobis(4-cyanopentanoic acid), 2,2-azobis[2-(2-imidazon-2-yl)propane]dihydrochloride, and benzoyl peroxide.

30. The method according to claim 22 wherein in the disposing step (a), the disposing step (c), or both the steps (a) and (c), the polymerization initiator is independently selected for each surface portion and is selected from the group consisting of a tetrakis (4-benzoylbenzyl ether) of pentaerythritol and a tetrakis (4-benzoylbenzoate ester) of pentaerythritol.

31. The method according to claim 22 wherein in the disposing step (a), the disposing step (c), or both the steps (a) and (c), the polymerization initiator is independently selected for each surface portion and is selected from the group consisting of 4,5-bis(4-benzoylphenylmethyleneoxy)benzene-1,3-disulfonic acid dipotassium salt, 4,5-bis(4-benzoylphenylmethyleneoxy)benzene-1,3-disulfonic acid disodium salt, 2,5-bis-(4-benzoylphenylmethyleneoxy)benzene-1,4-disulfonic acid dipotassium salt, 2,5-bis-(4-benzoylphenylmethyleneoxy)benzene-1,4-disulfonic acid disodium salt, 2,5-bis(4-benzoylphenylmethyleneoxy)benzene-1-disulfonic acid monopotassium salt, 2,5-bis(4-benzoylphenylmethyleneoxy)benzene-1-disulfonic acid monosodium salt, and combinations of any of these.

32. The method according to claim 22 wherein the disposing step (a) comprises disposing a first composition comprising a first biocompatible agent including one or more photoreactive groups.

33. The method according to claim 22 wherein the disposing step (a) comprises disposing a first composition comprising biocompatible agent including one or more polymerizable groups selected from the group consisting of vinyl groups, (meth)acrylamide groups, and (meth or eth)acrylate groups.

34. The method according to claim 22 wherein the disposing step (c) comprises disposing a second composition comprising a second biocompatible agent including one or more photoreactive groups.

35. The method according to claim 22 wherein the disposing step (c) comprises disposing a second composition comprising a second biocompatible agent including one or more polymerizable groups selected from the group consisting of vinyl groups, (meth)acrylamide groups, and (meth or eth) acrylate groups.

36. The method according to claim 22 wherein each disposing step of the method is independently accomplished by immersion coating, and spray coating.

\* \* \* \* \*

UNITED STATES PATENT AND TRADEMARK OFFICE
CERTIFICATE OF CORRECTION

PATENT NO. : 8,377,461 B2
APPLICATION NO. : 11/295836
DATED : February 19, 2013
INVENTOR(S) : Joseph A. Chinn, Sean M. Stucke and Stephen J. Chudzik It is certified that error appears in the above-identified patent and that said Letters Patent is hereby corrected as shown below:

In the Claims:

Column 64,
Line 23, "are" should be --become covalently and non-releasably--

Column 64,
Line 26, "become covalently and non-releasably" should be --are--

Signed and Sealed this
Seventh Day of May, 2013

Teresa Stanek Rea
*Acting Director of the United States Patent and Trademark Office*